(12) United States Patent
Allen et al.

(10) Patent No.: US 7,569,726 B2
(45) Date of Patent: Aug. 4, 2009

(54) INDANONE DERIVATIVES THAT INHIBIT PROLYL HYDROXYLASE

(75) Inventors: Jennifer R. Allen, Newbury Park, CA (US); Roland Burli, Bishop's Shortford (GB); Jennifer E. Golden, Simi Valley, CA (US); Kristine M. Muller, Walnut Creek, CA (US); Anthony B. Reed, Oxnard, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/082,263

(22) Filed: Apr. 9, 2008

(65) Prior Publication Data

US 2009/0088475 A1 Apr. 2, 2009

Related U.S. Application Data

(60) Provisional application No. 60/925,318, filed on Apr. 18, 2007.

(51) Int. Cl.
C07C 257/00 (2006.01)
C07C 229/00 (2006.01)
A61K 31/195 (2006.01)

(52) U.S. Cl. .................. 564/252; 562/444; 514/563
(58) Field of Classification Search .............. None
See application file for complete search history.

(56) References Cited

U.S. PATENT DOCUMENTS

| | | | |
|---|---|---|---|
| 3,954,733 | A | 5/1976 | Tobiki et al. |
| 3,992,371 | A | 11/1976 | Tobiki et al. |
| 4,215,123 | A | 7/1980 | Scotese et al. |
| 4,374,138 | A | 2/1983 | Haskell et al. |
| 4,382,089 | A | 5/1983 | Haskell et al. |
| 4,404,201 | A | 9/1983 | Haskell et al. |
| 4,468,394 | A | 8/1984 | Machida et al. |
| 4,710,473 | A | 12/1987 | Morris |
| 5,037,826 | A | 8/1991 | Blythin et al. |
| 5,126,341 | A | 6/1992 | Suzuki et al. |
| 5,378,679 | A | 1/1995 | Nuebling et al. |
| 5,502,035 | A | 3/1996 | Haviv et al. |
| 5,620,995 | A | 4/1997 | Weidmann et al. |
| 5,719,164 | A | 2/1998 | Weidmann et al. |
| 5,798,451 | A | 8/1998 | von Deyn et al. |
| 5,972,841 | A | 10/1999 | von Deyn et al. |
| 6,093,730 | A | 7/2000 | Weidmann et al. |
| 6,593,343 | B2 | 7/2003 | Björk et al. |
| 6,787,326 | B1 | 9/2004 | Ratcliffe et al. |
| 2003/0153503 | A1 | 8/2003 | Klaus et al. |
| 2004/0235082 | A1 | 11/2004 | Fourney et al. |
| 2004/0254215 | A1 | 12/2004 | Arend et al. |
| 2005/0020487 | A1 | 1/2005 | Klaus et al. |
| 2005/0107364 | A1 | 5/2005 | Hutchinson et al. |
| 2006/0216295 | A1 | 9/2006 | Crabtree et al. |
| 2006/0251638 | A1 | 11/2006 | Guenzler-Pukall et al. |
| 2006/0276477 | A1 | 12/2006 | Klaus et al. |
| 2007/0004627 | A1 | 1/2007 | Seeley et al. |
| 2007/0203174 | A1 | 8/2007 | Klimko et al. |
| 2007/0249605 | A1 | 10/2007 | Allen et al. |
| 2008/0171756 | A1 | 7/2008 | Shaw et al. |

FOREIGN PATENT DOCUMENTS

| | | |
|---|---|---|
| AT | 328085 | 3/1976 |
| EP | 0 500 297 A1 | 8/1992 |
| EP | 0 503 844 A1 | 9/1992 |
| EP | 0 937 459 A2 | 8/1999 |
| EP | 0 547 708 B1 | 2/2003 |
| EP | 1 541 558 A1 | 8/2003 |
| EP | 1 538 160 A1 | 6/2005 |
| GB | 1 449 256 | 9/1976 |
| JP | 493592 A | 4/1974 |
| JP | 7224040 A2 | 8/1995 |
| SU | 1735288 | 5/1992 |
| WO | WO 01/85732 A1 | 11/2001 |
| WO | WO 02/076396 A2 | 10/2002 |
| WO | WO 03/053997 A2 | 7/2003 |
| WO | WO 2004/037853 A2 | 5/2004 |
| WO | WO 2004/103974 A1 | 12/2004 |
| WO | WO 2004/104000 A1 | 12/2004 |
| WO | WO 2004/108121 A1 | 12/2004 |
| WO | WO 2004/108681 A1 | 12/2004 |
| WO | WO 2005/011696 A1 | 2/2005 |
| WO | WO 2005/021546 A1 | 3/2005 |
| WO | WO 2005/047285 A1 | 5/2005 |
| WO | WO 2005/077050 A2 | 8/2005 |
| WO | WO 2005/111044 A1 | 11/2005 |
| WO | WO 2006/088246 A1 | 8/2006 |

(Continued)

OTHER PUBLICATIONS

U.S. Appl. No. 12/002,537, filed Dec. 17, 2007, Allen et al.
U.S. Appl. No. 12/002,538, filed Dec. 17, 2007, Allen et al.
U.S. Appl. No. 12/148,179, filed Apr. 16, 2008, Allen et al.
U.S. Appl. No. 12/150,675, filed Apr. 29, 2008, Allen et al.
U.S. Appl. No. 12/150,998, filed May 2, 2008, Allen et al.

(Continued)

*Primary Examiner*—Sikarl A Witherspoon
(74) *Attorney, Agent, or Firm*—Bernard Friedrichsen

(57) ABSTRACT

Compounds of Formula I are useful inhibitors of HIF prolyl hydroxylases. Compounds of Formula I have the following structure:

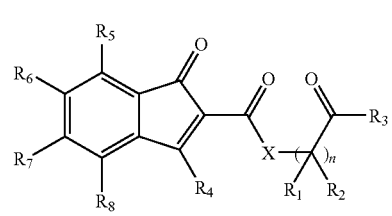

where the definitions of the variables are provided herein.

23 Claims, 3 Drawing Sheets

FOREIGN PATENT DOCUMENTS

| | | |
|---|---|---|
| WO | WO 2006/094292 A2 | 9/2006 |
| WO | WO 2007/038571 A2 | 4/2007 |
| WO | WO 2007/070359 A2 | 6/2007 |
| WO | WO 2007/097929 A1 | 8/2007 |
| WO | WO 2007/103905 A2 | 9/2007 |
| WO | WO 2007/136990 A2 | 11/2007 |
| WO | WO 2007/150011 A2 | 12/2007 |
| WO | WO 2008/040002 A2 | 4/2008 |

OTHER PUBLICATIONS

International Search Report and Written Opinion from co-pending PCT Application No. PCT/US2008/004634 mailed on Sep. 1, 2008.

He, L. et al., "Probabilistic Neural Network Multiple Classifier System for Predicting the Genotoxicity of Quinolones and Quinoline Derivatives," Chem. Res. Toxicol. 18, pp. 428-440 (2005).

Ukrainets, I.V. et al., "4-Hydroxy-2-Quinolines. XXI. 1H-2-Oxo-4-Hydroxyquinoline-3-Carboxylic Alkylamides as a Novel Group of Antithyroid Drugs," Farmatsevtichnii Zhurnal (Kiev) 6, pp. 54-55 (1995).

Bezuglyi, P.A., "Amides of 4-Hydroxyquinoline-2-oxo-3-carboxylic Acid: Synthesis and Anticoagulant Activity," Khimiko-Farmatsevticheskii Zhurnal, 24(4) pp. 31-32 (1990). This document is in the Russian language-an English language abstract is included.

Schofield, C.J. et al., "Oxygen Sensing by HIF Hydroxylases", Nature Reviews, Molecular Cell Biology, 5(5), pp. 243-254 (2004).

McDowell, R. S. et al., "From Peptide to Non-Peptide. 2. The De Novo Design of Potent, Non-peptidal Inhibitors of Platelet Aggregation Based on a Benzodiazepinedione Scaffold," J. Am. Chem. Soc. 116(12) pp. 5077-5083 (1994).

Bohnert et al., "Redox Reactions with Cyclopeptide-Like Quinoline Derivatives as Lipophilic, Masked NAD Model Compounds," Zeitschrift für Naturforschung, B.: Chemical Sciences, 42(9) pp. 1159-1166 (1987). This document is in the German language-an English language abstract is included.

Kath, J.C. et al., Potent Small Molecule CCR1 Antagonists, Bioorg & Med. Chem. Letters, 14(9), pp. 2169-2173 (2004).

Ukrainets, I.V. et al., "4-Hydroxy-2-Quinolones. 4. Selection of the Optimum Path for Synthesis of N-R-Substituted 4-Hydroxy-2-Quinolone-3-Carboxylic Acid Amides." Chemistry of Heterocyclic Compounds 28(5), pp. 538-540 (1992).

Warshakoon, N.C. et al., "Design and Synthesis of a Series of Novel Pyrazolopyridines as HIF 1-α Prolyl Hydroxylase Inhibitors," Bioorg & Med. Chem. Letters, 16, pp. 5687-5690 (2006).

Warshakoon, N.C. et al., "Structure-Based Design, Synthesis, and SAR Evaluation of a New Series of 8-Hydroxyquinolinse as HIF-1α Prolyl Hydroxylase Inhibitors," Bioorg & Med. Chem. Letters, 16, pp. 5517-5522 (2006).

Warshakoon, N.C. et al., "A Novel Series of Imidazo[1,2-a]pyridine Derivatives as HIF-1α Prolyl Hydroxylase Inhibitors," Bioorg & Med. Chem. Letters, 16, pp. 5598-5601 (2006).

McDonough, M.A. et al., "Cellular Oxygen Sensing: Crystal Structure of Hypoxia-Inducible Factor Prolyl Hydroxylase (PHD2)," Proc. Natl. Acad. Sci., 103(26) pp. 9814-9819 (2006).

Jönssen, S. et al., "Synthesis and Biological Evaluation of New 1,2-Dihydro-4-hydroxy-2-oxo-3-quinolinecarboxamides for Treatment of Autoimmune Diorders: Structure-Activity Relationship," J. Med. Chem. 47, pp. 2075-2088 (2004).

Buckle, D.R. et al., "Synthesis and Antiallergic Activity of 2-Hydroxy-3-nitro-1,4-naphthoquinones," J. Med. Chem. 20(8), pp. 1059-1064 (1977).

Franklin, T.J. et al., "Approaches to the Design of Anti-Fibrotic Drugs," Biochem. Soc. Trans. 19, pp. 812-815 (1991).

SEQUENCE LISTING

```
<160> NUMBER OF SEQ ID NOS: 7

<210> SEQ ID NO 1
<211> LENGTH: 166
<212> TYPE: PRT
<213> ORGANISM: Homo sapiens

<400> SEQUENCE: 1

Met His His His His His His Glu Ala Gly Arg Pro Arg Pro Val Leu
1               5                   10                  15

Arg Ser Val Asn Ser Arg Glu Pro Ser Gln Val Ile Phe Cys Asn Arg
            20                  25                  30

Ser Pro Arg Val Val Leu Pro Val Trp Leu Asn Phe Asp Gly Glu Pro
        35                  40                  45

Gln Pro Tyr Pro Thr Leu Pro Pro Gly Thr Gly Arg Arg Ile His Ser
    50                  55                  60

Tyr Arg Gly His Leu Trp Leu Phe Arg Asp Ala Gly Thr His Asp Gly
65                  70                  75                  80

Leu Leu Val Asn Gln Thr Glu Leu Phe Val Pro Ser Leu Asn Val Asp
                85                  90                  95
```

Gly Gln Pro Ile Phe Ala Asn Ile Thr Leu Pro Val Tyr Thr Leu Lys
100                 105                 110

Glu Arg Cys Leu Gln Val Val Arg Ser Leu Val Lys Pro Glu Asn Tyr
115                 120                 125

Arg Arg Leu Asp Ile Val Arg Ser Leu Tyr Glu Asp Leu Glu Asp His
130                 135                 140

Pro Asn Val Gln Lys Asp Leu Glu Arg Leu Thr Gln Glu Arg Ile Ala
145                 150                 155                 160

His Gln Arg Met Gly Asp
165

<210> SEQ ID NO 2
<211> LENGTH: 118
<212> TYPE: PRT
<213> ORGANISM: Homo sapiens

<400> SEQUENCE: 2

Met Asp Val Phe Leu Met Ile Arg Arg His Lys Thr Thr Ile Phe Thr
1               5                   10                  15

Asp Ala Lys Glu Ser Ser Thr Val Phe Glu Leu Lys Arg Ile Val Glu
20                  25                  30

Gly Ile Leu Lys Arg Pro Pro Asp Glu Gln Arg Leu Tyr Lys Asp Asp
35                  40                  45

Gln Leu Leu Asp Asp Gly Lys Thr Leu Gly Glu Cys Gly Phe Thr Ser
50                  55                  60

Gln Thr Ala Arg Pro Gln Ala Pro Ala Thr Val Gly Leu Ala Phe Arg
65                  70                  75                  80

Ala Asp Asp Thr Phe Glu Ala Leu Cys Ile Glu Pro Phe Ser Ser Pro
85                  90                  95

Pro Glu Leu Pro Asp Val Met Lys Pro Gln Asp Ser Gly Ser Ser Ala
100                 105                 110

Asn Glu Gln Ala Val Gln
115

<210> SEQ ID NO 3
<211> LENGTH: 96
<212> TYPE: PRT
<213> ORGANISM: Homo sapiens

<400> SEQUENCE: 3

Met Tyr Val Lys Leu Ile Ser Ser Asp Gly His Glu Phe Ile Val Lys
1               5                   10                  15

Arg Glu His Ala Leu Thr Ser Gly Thr Ile Lys Ala Met Leu Ser Gly
20                  25                  30

Pro Gly Gln Phe Ala Glu Asn Glu Thr Asn Glu Val Asn Phe Arg Glu
35                  40                  45

Ile Pro Ser His Val Leu Ser Lys Val Cys Met Tyr Phe Thr Tyr Lys
50                  55                  60

Val Arg Tyr Thr Asn Ser Ser Thr Glu Ile Pro Glu Phe Pro Ile Ala
65                  70                  75                  80

Pro Glu Ile Ala Leu Glu Leu Leu Met Ala Ala Asn Phe Leu Asp Cys
85                  90                  95

<210> SEQ ID NO 4
<211> LENGTH: 20
<212> TYPE: PRT
<213> ORGANISM: Artificial Sequence
<220> FEATURE:

```
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation
<220> FEATURE:
<221> NAME/KEY: MISC_FEATURE
<222> LOCATION: (20)..(20)
<223> OTHER INFORMATION: Carboxylation

<400> SEQUENCE: 4

Asp Leu Asp Leu Glu Ala Leu Ala Pro Tyr Ile Pro Ala Asp Asp
1               5                   10                  15

Phe Gln Leu Arg
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation
<220> FEATURE:
<221> NAME/KEY: MISC_FEATURE
<222> LOCATION: (9)..(9)
<223> OTHER INFORMATION: Xaa at position 9 is hydroxyproline
<220> FEATURE:
<221> NAME/KEY: MISC_FEATURE
<222> LOCATION: (20)..(20)
<223> OTHER INFORMATION: Carboxyamidated

<400> SEQUENCE: 5

Asp Leu Asp Leu Glu Ala Leu Ala Xaa Tyr Ile Pro Ala Asp Asp
1               5                   10                  15

Phe Gln Leu Arg
            20

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Asp Leu Glu Met Leu Ala Pro Tyr Ile Pro Met Asp Asp Asp Phe Gln
1               5                   10                  15

Leu

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Biotinylation

<400> SEQUENCE: 7

Asp Leu Glu Met Leu Ala Pro Tyr Ile Pro Met Asp Asp Asp Phe Gln
1               5                   10                  15

Leu
```

INDANONE DERIVATIVES THAT INHIBIT PROLYL HYDROXYLASE

CROSS REFERENCES TO RELATED APPLICATIONS

This application claims the benefit of U.S. Provisional Application No. 60/925,318, filed on Apr. 18, 2007, which is hereby incorporated by reference in its entirety and for all purposes as if fully set forth herein.

FIELD OF THE INVENTION

The present invention relates to compounds capable of inhibiting prolyl hydroxylases such as HIF prolyl hydroxylases, compounds that modulate HIF levels, compounds that stabilize HIF, compositions comprising the compounds, and methods for their use for controlling HIF levels. The compounds and compositions may be used to treat diseases or conditions modulated by HIF such as ischemia, anemia, wound healing, auto-transplantation, allo-transplantation, xeno-transplantation, systemic high blood pressure, thalassemia, diabetes, cancer, and inflammatory disorders.

BACKGROUND OF THE INVENTION

The cellular transcription factor HIF (Hypoxia Inducible Factor) occupies a central position in oxygen homeostasis in a wide range of organisms and is a key regulator of responses to hypoxia. The genes regulated by HIF transcriptional activity can play critical roles in angiogenesis, erythropoiesis, hemoglobin F production, energy metabolism, inflammation, vasomotor function, apoptosis and cellular proliferation. HIF can also play a role in cancer, in which it is commonly upregulated, and in the pathophysiological responses to ischemia and hypoxia.

The HIF transcriptional complex comprises an αβ heterodimer: HIF-β is a constitutive nuclear protein that dimerizes with oxygen-regulated HIF-α subunits. Oxygen regulation occurs through hydroxylation of the HIF-α subunits, which are then rapidly destroyed by the proteasome. In oxygenated cells, the von Hippel-Lindau tumor suppressor protein (pVHL) binds to hydroxylated HIF-α subunits, thereby promoting their ubiquitin dependent proteolysis. This process is suppressed under hypoxic conditions, stabilizing HIF-α and promoting transcriptional activation by the HIF αβ complex. See, e.g., U.S. Pat. No. 6,787,326.

Hydroxylation of HIF-α subunits can occur on proline and asparagine residues and can be mediated by a family of 2-oxoglutarate dependent enzymes. This family includes the HIF prolyl hydroxylase isozymes (PHDs), which hydroxylate Pro 402 and Pro 564 of human HIF1α, as well as Factor Inhibiting HIF (FIH), which hydroxylates Asn 803 of human HIF1α. Inhibition of FIH or the PHDs leads to HIF stabilization and transcriptional activation. See, e.g., Schofield and Ratcliffe, Nature Rev. Mol. Cell. Biol., Vol 5, pages 343-354 (2004).

SUMMARY OF THE INVENTION

In one aspect, the invention provides at least one compound of Formula I:

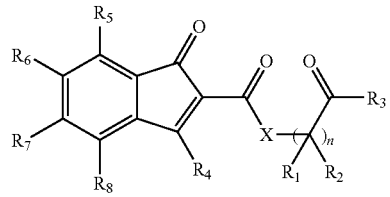

a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

n is 1 to 6;

X is $-NR_a-$, wherein $R_a$ is H;

each instance of $R_1$ and $R_2$ is independently selected from H, lower alkyl, substituted lower alkyl, lower haloalkyl, or substituted lower haloalkyl, or $R_1$ and $R_2$, together with the carbon to which they are attached, can join to form a 3-6 membered optionally substituted ring comprising 0, 1, or 2 heteroatoms selected from O, N, and S;

$R_3$ is selected from OH, SH, $NH_2$, lower alkyl, substituted lower alkyl, lower alkoxy, substituted lower alkoxy, or sulfanyl;

$R_4$ is OH;

$R_5$, $R_6$, $R_7$, and $R_8$ are independently selected from H, Cl, F, Br, I, alkyl, substituted alkyl, alkenyl, substituted alkenyl, alkynyl, substituted alkynyl, $NR_bR_c$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, haloalkyl, perhaloalkyl, or $-Y-R_{10}$, wherein:

Y is selected from $-N(R_{11})-Z-$ or $-Z-N(R_{11})-$;

Z is selected from C(O), $SO_2$, alkylene, substituted alkylene, alkenylene, substituted alkenylene, alkynylene, or substituted alkynylene;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl or substituted heteroaryl;

$R_{11}$ is selected from H, lower alkyl, or substituted lower alkyl; and $R_b$ and $R_c$ are independently selected from H, lower alkyl, substituted lower alkyl, lower haloalkyl, or substituted lower haloalkyl, or $R_b$ and $R_c$, can join together to form a 3 to 6 membered ring or a substituted 3 to 6 membered ring.

In some embodiments of the compound of Formula I, $R_3$ is OH.

In some embodiments of the compound of Formula I, at least one instance of $R_5$, $R_6$, $R_7$, or $R_8$ is a substituted or unsubstituted aryl, a substituted or unsubstituted heteroaryl, a substituted or unsubstituted cycloalkyl, or a substituted or unsubstituted heterocyclyl group. In some such embodiments, at least one instance of $R_5$, $R_6$, $R_7$, or $R_8$ is a heterocyclyl group. In other such embodiments, at least one instance of $R_5$, $R_6$, $R_7$, or $R_8$ is a heteroaryl group. In other such embodiments, at least one instance of $R_5$, $R_6$, $R_7$, or $R_8$ is a phenyl or substituted phenyl group.

In some embodiments of the compound of Formula I, at least one instance of $R_5$, $R_6$, $R_7$, or $R_8$ is chosen from a halo or a moiety substituted with at least one halo. For example, in some embodiments, at least one instance of $R_5$, $R_6$, $R_7$, or $R_8$ is a haloalkyl or perhaloalkyl group. In some such embodiments, at least one instance of $R_5$, $R_6$, $R_7$, or $R_8$ is a perfluoroalkyl group such as a $CF_3$ group.

In some embodiments of the compound of Formula I, at least one instance of $R_5$, $R_6$, $R_7$, or $R_8$ is other than H. In some embodiments, at least two instances of $R_5$, $R_6$, $R_7$, or $R_8$ are other than H.

In some embodiments of the compound of Formula I, n is 1.

In some embodiments of the compound of Formula I, n is 1 and $R_3$ is OH or a salt or prodrug thereof. In some such embodiments, $R_1$ and $R_2$ are both H.

In some embodiments of the compound of Formula I, $R_1$ and $R_2$ are independently selected from H and lower alkyl. In some such embodiments, $R_1$ and $R_2$ are independently selected from H and methyl. In some such embodiments, $R_1$ and $R_2$ are both H.

In some embodiments, the at least one compound is a salt. Such salts may be anhydrous or associated with water as a hydrate.

In some embodiments, the compound is a prodrug. In some such embodiments, the compound is a $(C_1-C_6)$alkyl ester such as a methyl, ethyl, propyl, butyl, pentyl, or hexyl ester.

Also provided herein are pharmaceutical compositions that include at least one pharmaceutically acceptable carrier, and a therapeutically effective amount of at least one compound of any of the embodiments described herein. In such embodiments, the at least one compound is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

In some embodiments, the invention provides a pharmaceutical composition that includes a compound of any of the embodiments in an amount effective for increasing the amount of erythropoietin in the blood of a subject.

Further provided are pharmaceutical compositions that include at least one pharmaceutically acceptable carrier, and a therapeutically effective amount of at least one compound of any of the embodiments described herein in combination with at least one additional compound such as an erythropoiesis stimulating agent or a chemotherapeutic agent.

Additionally provided is a method of increasing or stabilizing HIF levels or activity in a subject by administering to the subject at least one compound of any of the embodiments described herein.

Further provided is a method of treating a condition where it is desired to modulate HIF activity comprising administering to a subject at least one compound of any of the embodiments described herein. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

Also provided is a method of treating a hypoxic or ischemic related disorder in a subject comprising administering to a subject at least one compound of any of the embodiments described herein.

Also provided is a method of treating anemia in a subject comprising administering to a subject at least one compound of any of the embodiments described herein.

Also provided is a method for increasing the amount of erythropoietin in the blood or plasma of a subject. Such methods include administering a therapeutically effective amount of the compound of any one of the embodiments to the subject.

Further provided is a method of modulating the amount of HIF in a cell comprising contacting the cell with at least one compound of any of the embodiments described herein.

Additionally provided is a method of increasing the amount of hemoglobin F in a subject comprising administering to the subject at least one compound of any of the embodiments described herein.

Also provided is a method of modulating angiogenesis in a subject comprising administering to the subject at least one compound of any of the embodiments described herein.

Additionally provided is a method of treating at least one disease in a patient in need of such treatment comprising administering to the patient a therapeutically effective amount of at least one compound of any of the embodiments described herein. In some such embodiments, the at least one disease is selected from ischemia, anemia, wound healing, auto-transplantation, allo-transplantation, xeno-transplantation, systemic high blood pressure, thalassemia, diabetes, cancer, or an inflammatory disorder.

Also provided is a method of inhibiting HIF hydroxylation in a subject comprising administering to the subject at least one compound of any of the embodiments described herein.

In some embodiments, the HIF PHD inhibitory activity $IC_{50}$ value of the compound is 40 µM or less. In other embodiments, the HIF PHD inhibitory activity $IC_{50}$ value of the compound is 10 µM or less.

In some embodiments, the at least one compound of any of the embodiments is used in the preparation of a medicament.

In some such embodiments, the at least one compound of any of the embodiments is used in the preparation of a medicament for increasing or stabilizing HIF levels or activity in a subject.

In some such embodiments, the at least one compound of any of the embodiments is used in the preparation of a medicament for treating a condition where it is desired to modulate HIF activity. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

In some embodiments, the at least one compound of any of the embodiments is used in the preparation of a medicament for treating a hypoxic or ischemic related disorder in a subject.

In some embodiments, the at least one compound of any of the embodiments is used in the preparation of a medicament for modulating the amount if HIF in a cell. In some embodiments, the at least one compound according to any of the embodiments is used to modulate the amount of HIF in a cell.

In some embodiments, the at least one compound of any of the embodiments is used in the preparation of a medicament for modulating angiogenesis in a subject.

In some embodiments, the at least one compound of any of the embodiments is used in the preparation of a medicament for inhibiting HIF hydroxylation in a subject.

In some embodiments, the at least one compound of any of the embodiments is used in the preparation of a medicament for treating anemia.

Other objects, features and advantages of the invention will become apparent to those skilled in the art from the following description and claims.

BRIEF DESCRIPTION OF THE DRAWINGS

FIG. 2A illustrates a 0-125 nM peptide range and FIG. 2B illustrates a 0-10 nM peptide range.

FIG. 3A illustrates a time course for the hydroxylation of the HIF1α peptide with increasing amounts of HIF PHD2 enzyme. FIG. 3B illustrates initial rates with increasing enzyme concentrations.

DETAILED DESCRIPTION OF THE INVENTION

Figure 1:
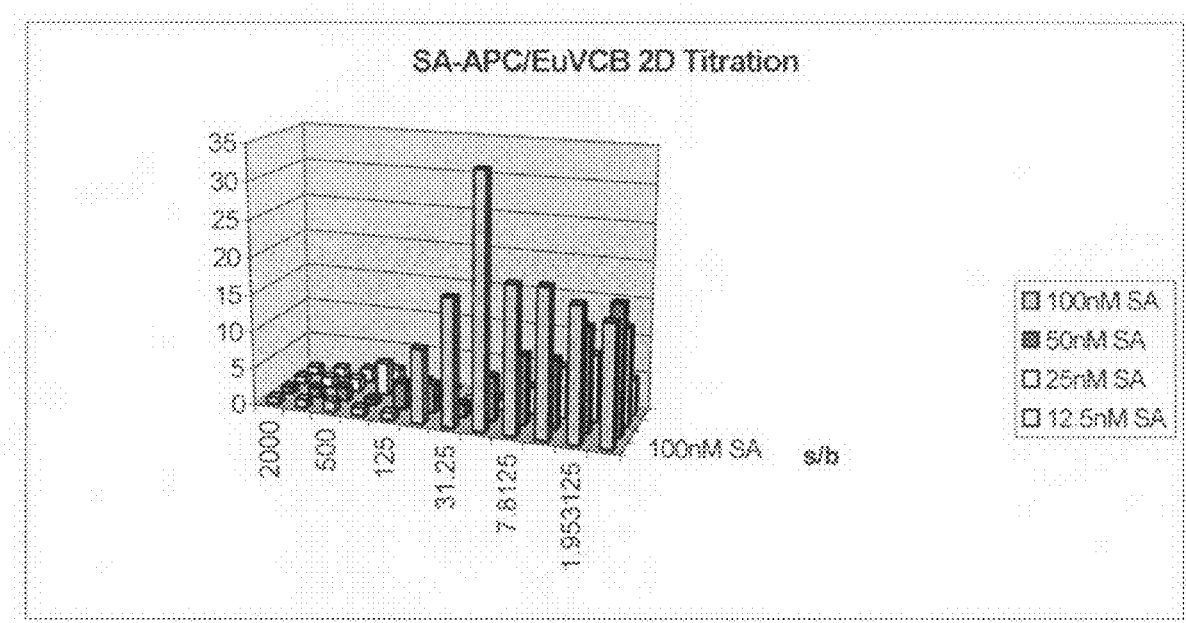
FIG. 1 is a graph illustrating the ratio of fluorescence signal to background generated by the interaction of Eu-VCB with streptavidin-APC-hydroxyprolyl HIF1α peptide.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Compounds of Formula I include, but are not limited to, optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with double bonds.

Compounds of the invention may exist in multiple tautomeric forms. These forms are illustrated below as "Tautomer A", "Tautomer B", and "Tautomer C":

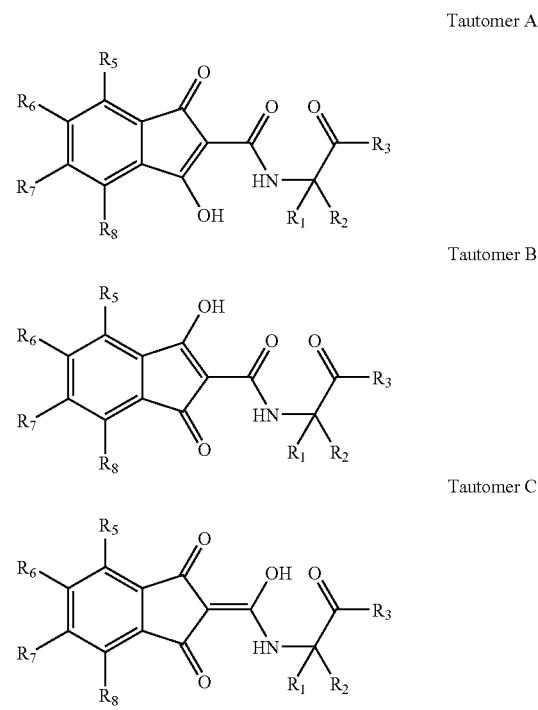

Tautomer A

Tautomer B

Tautomer C

Compounds of the invention are depicted structurally and named as compounds in the "Tautomer A" form. However, it is specifically contemplated that the compounds may also exist in "Tautomer B" and "Tautomer C" form and compounds in "Tautomer B" and "Tautomer C" form or another tautomeric form are expressly considered to be part of the invention and included within the claimed invention.

Compounds of the present disclosure include, but are not limited to, compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing.

As noted above, prodrugs also fall within the scope of chemical entities, for example, ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, benzoate, carbomethoxy, carboethoxy and like derivatives of functional groups (such as alcohol, carboxylic acid, ether, ester, or amine groups) in the compounds of Formula I. In some embodiments, the prodrugs of the compounds of Formula I are esters such as methyl, ethyl, propyl, butyl, pentyl, and hexyl esters.

The term "solvate" refers to the compound formed by the interaction of a solvent and a compound. Suitable solvates are pharmaceutically acceptable solvates, such as hydrates, including monohydrates and hemi-hydrates.

"Alkyl" refers to a saturated, branched, straight-chain, or cyclic monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. In certain embodiments, an alkyl group comprises from 1 to 20 carbon atoms. As used herein the term "lower alkyl" refers to an alkyl group comprising from 1 to 6 carbon atoms.

"Alkenyl" refers to an unsaturated branched, straight-chain, or cyclic hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms, i.e. "lower alkenyl."

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl; 2-pentynyl, 3-pentynyl, 2-hexynyl, 3-hexynyl and the like. In certain embodiments, an alkynyl group has from 2 to 20 carbon atoms and in other embodiments, from 2 to 6 carbon atoms, i.e. "lower alkynyl."

"Alkoxy" refers to a radical —OR where R represents an alkyl group as defined herein. Representative examples include, but are not limited to, methoxy, ethoxy, propoxy, butoxy, cyclohexyloxy, and the like. Typical alkoxy groups include from 1 to 10 carbon atoms, from 1 to 6 carbon atoms or from 1 to 4 carbon atoms in the R group. Lower alkoxy groups include ($C_{1-6}$) alkyl groups and, in some embodiments, may include ($C_{1-4}$) alkyl groups.

"Alkoxycarbonyl" refers to a radical —C(O)—OR where R is as defined above with respect to "Alkoxy".

"Alkylene" refers to a divalent saturated hydrocarbon group derived from a parent alkane by removal of two hydrogen atoms. Examples of alkylene group include, but are not limited to, —CH$_2$—, —CH$_2$CH$_2$—, —CH(CH$_3$)—, —CH$_2$CH$_2$CH$_2$—, —CH$_2$C(CH$_3$)(H)—, and the like.

"Alkenylene" refers to a divalent unsaturated hydrocarbon group having at least one carbon-carbon double bond derived by the removal of two hydrogen atoms from a parent alkene. The group may be in either the Z- or E-form (cis or trans) about the double bond(s). Examples of alkenylene groups, include, but are not limited to, —CH═CH—, —CH═C(H)CH$_2$—, —CH$_2$C(H)═C(H)CH$_2$—, and the like.

"Alkynylene" refers to a divalent unsaturated hydrocarbon group having at least one carbon-carbon triple bond derived by the removal of two hydrogen atoms from a parent alkyne. Example of alkynylene groups, include, but are not limited to, —C≡C—, —CH$_2$C≡C—, —CH$_2$C≡CCH$_2$—.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. For example, aryl includes 5- and 6-membered carbocyclic aromatic rings fused to a 5- to 7-membered heterocyclic ring containing 1 or more heteroatoms chosen from N, O, and S. In certain embodiments, an aryl group can comprise from 6 to 10 carbon atoms. Aryl, however, does not encompass or overlap in any way with heteroaryl, separately defined below. Hence, if one or more carbocyclic aromatic rings is fused with a heterocyclic aromatic ring, the resulting ring system is heteroaryl, not aryl, as defined herein.

"Arylalkyl" or "aralkyl" refers to an acyclic alkyl group in which one of the hydrogen atoms bonded to a carbon atom, typically, but not necessarily, a terminal carbon atom, is replaced with an aryl group. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. In certain embodiments, an arylalkyl group can be ($C_{6-30}$) arylalkyl, e.g., the alkyl group of the arylalkyl group can be ($C_{1-10}$) and the aryl moiety can be ($C_{5-20}$).

"Arylalkenyl" refers to an alkenyl group in which a bond to one of the hydrogen atoms of the alkenyl group is replaced with a bond to an aryl group.

"Arylalkynyl" refers to an alkynyl group in which a bond to one of the hydrogen atoms of the alkynyl group is replaced with a bond to an aryl group.

"Carbonyl" refers to the radical —C(O) group.

"Carboxy" refers to the radical —C(O)OH.

"Cyano" refers to the radical —CN.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In certain embodiments, the cycloalkyl group can be $C_{3-10}$ cycloalkyl, such as, for example, $C_{3-6}$ cycloalkyl.

"Heterocyclic", "heterocyclo" or "heterocyclyl" refer to a saturated or unsaturated, but non-aromatic, cyclic hydrocarbon group in which one or more carbon atoms (and any associated hydrogen atoms) are independently replaced with the same or different heteroatom and its associated hydrogen atoms, where appropriate. Typical heteroatoms to replace the carbon atom(s) include, but are not limited to, N, O, and S. Typical heterocyclyl groups include, but are not limited to, groups derived from epoxides, imidazolidine, morpholine, piperazine, piperidine, pyrazolidine, pyrrolidine, quinuclidine, tetrahydrofuran, tetrahydropyran and the like. Substituted heterocyclyl also includes ring systems substituted with one or more oxo (═O) or oxide (—O$^-$) substituents, such as piperidinyl N-oxide, morpholinyl-N-oxide, 1-oxo-1-thiomorpholinyl and 1,1-dioxo-1-thiomorpholinyl.

"Heterocyclylalkyl" refers to an alkyl group in which one of the hydrogen atoms of the alkyl is replaced with a bond to a heterocyclyl group. Examples of heterocyclylalkyl groups, include, but are not limited to, morpholinylmethyl, morpholinylethyl, tetrahydrofuranylmethyl, piperidinylmethyl, and the like.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl encompasses 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic ring systems containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring or a carbocyclic aromatic ring and a 5- to 7-membered heteroaromatic ring fused to a 5- to 7-membered heterocyclic ring. For fused, bicyclic heteroaryl ring systems wherein only one of the rings contains one or more heteroatoms, the point of attachment may be at the heteroaromatic ring or the carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heteroarylalkyl" or "heteroaralkyl" refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl, and/or heteroarylalkynyl is used. In certain embodiments, the heteroarylalkyl group can be a 6 to 30 membered heteroarylalkyl, e.g., the alkyl moiety of the heteroarylalkyl can include 1 to 10 members and the heteroaryl moiety of the heteroarylalkyl can include from 5 to 20-members.

"Sulfonyl" refers to a radical —S(O)$_2$R where R is an alkyl, substituted alkyl, substituted cycloalkyl, substituted heterocyclyl, substituted aryl, or substituted heteroaryl group as defined herein. Representative examples include, but are not limited to, methylsulfonyl, ethylsulfonyl, propylsulfonyl, butylsulfonyl, and the like.

"Sulfanyl" refers to a radical —SR where R is an alkyl, substituted alkyl, substituted cycloalkyl, substituted heterocyclyl, substituted aryl, or substituted heteroaryl group as defined herein that may be optionally substituted as defined herein. Representative examples include, but are not limited to, methylthio, ethylthio, propylthio, butylthio, and the like.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, —X, —R$_{11}$, —OH, =O, —OR$_{11}$, —SR$_{11}$, —SH, =S, —NR$_{11}$R$_{12}$, =NR$_{11}$, —CX$_3$, —CF$_3$, —CN, —NO$_2$, —S(O)$_2$R$_{11}$, —OS(O$_2$)OH, —OS(O)$_2$R$_{11}$, —OP(O)(OR$_{11}$)(OR$_{12}$), —C(O)R$_{11}$, —C(S)R$_{11}$, —C(O) OR$_{11}$, —C(O)NR$_{11}$R$_{12}$, —C(O)OH, —C(S)OR$_{11}$, —NR$_{13}$C(O)NR$_{11}$R$_{12}$, —NR$_{13}$C(S)NR$_{11}$R$_{12}$, —NR$_{13}$C(NR$_{11}$)NR$_{11}$R$_{12}$, —C(NR$_{11}$)NR$_{11}$R$_{12}$, —S(O)$_2$NR$_{11}$R$_{12}$, —NR$_{13}$S(O)$_2$R$_{11}$, —NR$_{13}$C(O)R$_{11}$, and —S(O) R$_{11}$ where each X is independently a halo; each R$_{11}$ and R$_{12}$ are independently hydrogen, alkyl, substituted alkyl, alkyl interrupted by one or more —O— or —S— groups, aryl, substituted aryl, arylalkyl, substituted arylalkyl, cycloalkyl, substituted cycloalkyl, heterocyclyl, substituted heterocyclyl, heteroaryl, substituted heteroaryl, heteroarylalkyl, substituted heteroarylalkyl, —NR$_{13}$R$_{14}$, —C(O)R$_{13}$ or —S(O)$_2$R$_{13}$ or optionally R$_{11}$ and R$_{12}$ together with the atom to which R$_{11}$ and R$_{12}$ are attached form one or more heterocyclyl, substituted heterocyclyl, heteroaryl, or substituted heteroaryl rings; and R$_{13}$ and R$_{14}$ are independently hydrogen, alkyl, substituted alkyl, aryl, substituted aryl, arylalkyl, substituted arylalkyl, cycloalkyl, substituted cycloalkyl, heterocyclyl, substituted heterocyclyl, heteroaryl, substituted heteroaryl, heteroarylalkyl or substituted heteroarylalkyl, or optionally $R_{13}$ and $R_{14}$ together with the nitrogen atom to which $R_{13}$ and $R_{14}$ are attached form one or more heterocyclyl, substituted heterocyclyl, heteroaryl, or substituted heteroaryl rings. In certain embodiments, a tertiary amine or aromatic nitrogen may be substituted with on or more oxygen atoms to form the corresponding nitrogen oxide.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

In one aspect, the invention provides at least one compound of Formula I:

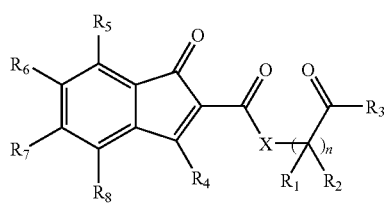

I a pharmaceutically acceptable salt thereof, a tautomer thereof, or a pharmaceutically acceptable salt of the tautomer; or a solvate thereof, a chelate thereof, a non-covalent complex thereof, a prodrug thereof, or a mixture of any of the foregoing, wherein:

n is 1 to 6;

X is $-NR_a-$, wherein $R_a$ is H;

each instance of $R_1$ and $R_2$ is independently selected from H, lower alkyl, substituted lower alkyl, lower haloalkyl, or substituted lower haloalkyl, or $R_1$ and $R_2$, together with the carbon to which they are attached, can join to form a 3-6 membered optionally substituted ring comprising 0, 1, or 2 heteroatoms selected from O, N, and S;

$R_3$ is selected from OH, SH, $NH_2$, lower alkyl, substituted lower alkyl, lower alkoxy, substituted lower alkoxy, or sulfanyl;

$R_4$ is OH;

$R_5$, $R_6$, $R_7$, and $R_8$ are independently selected from H, Cl, F, Br, I, alkyl, substituted alkyl, alkenyl, substituted alkenyl, alkynyl, substituted alkynyl, $NR_bR_c$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, haloalkyl, perhaloalkyl, or $-Y-R_{10}$, wherein:

Y is selected from $-N(R_{11})-Z-$ or $-Z-N(R_{11})-$;

Z is selected from C(O), $SO_2$, alkylene, substituted alkylene, alkenylene, substituted alkenylene, alkynylene, or substituted alkynylene;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl or substituted heteroaryl;

$R_{11}$ is selected from H, lower alkyl, or substituted lower alkyl; and $R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring.

In some embodiments of the compound of Formula I, $R_3$ is OH.

In some embodiments of the compound of Formula I, at least one of $R_5$, $R_6$, $R_7$, and $R_8$ is other than H. In some such embodiments, at least one of $R_5$, $R_6$, $R_7$, and $R_8$ is selected from Cl, F, Br, I, alkyl, substituted alkyl, alkenyl, substituted alkenyl, alkynyl, substituted alkynyl, $NR_bR_c$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, haloalkyl, perhaloalkyl, or $-Y-R_{10}$. In still other such embodiments, at least one of $R_5$, $R_6$, $R_7$, and $R_8$ is selected from Cl, F, Br, I, alkyl, $C(O)OR_9$, aryl, substituted aryl, heteroaryl, substituted heteroaryl, heterocyclyl, substituted heterocyclyl, haloalkyl, or perhaloalkyl. In still other such embodiments, at least one of $R_5$, $R_6$, $R_7$, and $R_8$ is selected from Cl, F, Br, I, aryl, substituted aryl, haloalkyl, or perhaloalkyl. In some embodiments, at least one of $R_5$, $R_6$, $R_7$, and $R_8$ is selected from Cl, F, Br, I, $CF_3$, phenyl, 4-methoxyphenyl, 3-methoxyphenyl, 2-methoxyphenyl, 4-chlorophenyl, 3-chlorophenyl, 2-chlorophenyl, 4-carboxyphenyl, 3-carboxyphenyl, 2-carboxyphenyl, cyclopropyl, 4-pyridyl, 3-pyridyl, 2-pyridyl, 3-thiophenyl, 2-thiophenyl, or 4-pyranyl. In still other embodiments, at least one, one, or two of $R_5$, $R_6$, $R_7$, and $R_8$ is selected from Cl, F, Br, I, aryl, substituted aryl, haloalkyl, or perhaloalkyl. In some embodiments, at least one of $R_5$, $R_6$, $R_7$, and $R_8$ is selected from Cl, F, Br, I, $CF_3$, phenyl, 4-methoxyphenyl, 3-methoxyphenyl, 2-methoxyphenyl, 4-chlorophenyl, 3-chlorophenyl, or 2-chlorophenyl. In some such embodiments, X is NH; n is 1, $R_1$ and $R_2$ are both H, and $R_4$ is OH. In some such embodiments, $R_3$ is OH or lower alkoxy such as a methoxy, ethoxy, propoxy, or butoxy group. In still other such embodiments, $R_3$ is OH.

In some embodiments of the compound of Formula I, at least one instance of $R_5$, $R_6$, $R_7$, or $R_8$ is a substituted or unsubstituted aryl, a substituted or unsubstituted heteroaryl, a substituted or unsubstituted cycloalkyl, or a substituted or unsubstituted heterocyclyl group. In some such embodiments, at least one instance of $R_5$, $R_6$, $R_7$, or $R_8$ is a heterocyclyl group. In other such embodiments, at least one instance of $R_5$, $R_6$, $R_7$, or $R_8$ is a heteroaryl group. In other such embodiments, at least one instance of $R_5$, $R_6$, $R_7$, or $R_8$ is a phenyl or substituted phenyl group.

In some embodiments of the compound of Formula I, at least one instance of $R_5$, $R_6$, $R_7$, or $R_8$ is chosen from a halo or a moiety substituted with at least one halo. For example, in some embodiments, at least one instance of $R_5$, $R_6$, $R_7$, or $R_8$ is a haloalkyl or perhaloalkyl group. In some such embodiments, at least one instance of $R_5$, $R_6$, $R_7$, or $R_8$ is a perfluoroalkyl group such as a $CF_3$ group.

In some embodiments of the compound of Formula I, at least one instance of $R_5$, $R_6$, $R_7$, or $R_8$ is other than H. In some embodiments, at least two instances of $R_5$, $R_6$, $R_7$, or $R_8$ are other than H. In some embodiments, the compound is other than 2-(3-hydroxy-1-oxo-1H-indene-2-carboxamido)acetic acid, or a methyl, ethyl, or propyl ester thereof.

In some embodiments of the compound of Formula I, at least one instance of $R_5$, $R_6$, $R_7$, or $R_8$ is chosen from any of the groups corresponding to these variables in any of the Example compounds.

In some embodiments of the compound of Formula I, n is 1.

In some embodiments of the compound of Formula I, n is 1 and $R_3$ is OH or a salt or prodrug thereof. In some such embodiments, $R_1$ and $R_2$ are both H.

In some embodiments of the compound of Formula I, X is —$NR_a$—; $R_a$ is H; n is 1; $R_1$ and $R_2$ are both H; $R_3$ is selected from OH or lower alkoxy; and $R_4$ is OH. In some such embodiments, at least one of $R_5$, $R_6$, $R_7$, and $R_8$ is other than H. In some embodiments, at least one of $R_5$, $R_6$, $R_7$, and $R_8$ is selected from Cl, F, Br, I, alkyl, substituted alkyl, alkenyl, substituted alkenyl, alkynyl, substituted alkynyl, $NR_bR_c$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, haloalkyl, perhaloalkyl, or —Y—$R_{10}$. In still other such embodiments, at least one of $R_5$, $R_6$, $R_7$, and $R_8$ is selected from Cl, F, Br, I, alkyl, $C(O)OR_9$, aryl, substituted aryl, heteroaryl, substituted heteroaryl, heterocyclyl, substituted heterocyclyl, haloalkyl, or perhaloalkyl. In still other such embodiments, at least one of $R_5$, $R_6$, $R_7$, and $R_8$ is selected from Cl, F, Br, I, aryl, substituted aryl, haloalkyl, or perhaloalkyl.

In some embodiments of the compound of Formula I, $R_1$ and $R_2$ are independently selected from H and lower alkyl. In some such embodiments, $R_1$ and $R_2$ are independently selected from H and methyl. In some embodiments, $R_1$ and $R_2$ are both H.

In one embodiment, the compound of Formula I is any one of the Example compounds described herein. Therefore, in some embodiments, the compound is selected from any one or all of those listed below or is a salt thereof, a tautomer thereof, or a salt of the tautomer:

2-(3-hydroxy-4-iodo-1-oxo-1H-indene-2-carboxamido)acetic acid;
2-(5-bromo-3-hydroxy-1-oxo-1H-indene-2-carboxamido)acetic acid;
2-(3-hydroxy-1-oxo-5-(trifluoromethyl)-1H-indene-2-carboxamido)acetic acid;
2-(4-chloro-3-hydroxy-1-oxo-1H-indene-2-carboxamido)acetic acid;
2-(6-fluoro-3-hydroxy-1-oxo-1H-indene-2-carboxamido)acetic acid;
2-(7-fluoro-3-hydroxy-1-oxo-1H-indene-2-carboxamido)acetic acid;
2-(4,7-dichloro-3-hydroxy-1-oxo-1H-indene-2-carboxamido)acetic acid;
2-(3-hydroxy-1-oxo-7-phenyl-1H-indene-2-carboxamido)acetic acid;
2-(3-hydroxy-1-oxo-6-phenyl-1H-indene-2-carboxamido)acetic acid;
2-(3-hydroxy-4-(4-methoxyphenyl)-1-oxo-1H-indene-2-carboxamido)acetic acid;
2-(3-hydroxy-5-(4-methoxyphenyl)-1-oxo-1H-indene-2-carboxamido)acetic acid;
2-(4-(4-chlorophenyl)-3-hydroxy-1-oxo-1H-indene-2-carboxamido)acetic acid;
2-(4-(3-chlorophenyl)-3-hydroxy-1-oxo-1H-indene-2-carboxamido)acetic acid;
2-(4-(2-chlorophenyl)-3-hydroxy-1-oxo-1H-indene-2-carboxamido)acetic acid;
2-(3-hydroxy-7-(2-methoxyphenyl)-1-oxo-1H-indene-2-carboxamido)acetic acid;
2-(3-hydroxy-7-(3-methoxyphenyl)-1-oxo-1H-indene-2-carboxamido)acetic acid;
2-(6-(2-chlorophenyl)-3-hydroxy-1-oxo-1H-indene-2-carboxamido)acetic acid; or
2-(3-hydroxy-6-(3-methoxyphenyl)-1-oxo-1H-indene-2-carboxamido)acetic acid.

In other embodiments, the compound is selected from any one or all of those listed below or is a salt thereof, a tautomer thereof, or a salt of the tautomer:

2-(5,6-dichloro-3-hydroxy-1-oxo-1H-indene-2-carboxamido)acetic acid;
2-(4,7-difluoro-3-hydroxy-1-oxo-1H-indene-2-carboxamido)acetic acid;
2-((carboxymethyl)carbamoyl)-3-hydroxy-1-oxo-1H-indene-4-carboxylic acid;
2-((carboxymethyl)carbamoyl)-3-hydroxy-1-oxo-1H-indene-5-carboxylic acid;
4-(2-((carboxymethyl)carbamoyl)-3-hydroxy-1-oxo-1H-inden-4-yl)benzoic acid;
4-(2-((carboxymethyl)carbamoyl)-3-hydroxy-1-oxo-1H-inden-5-yl)benzoic acid;
2-(5-(4-chlorophenyl)-3-hydroxy-1-oxo-1H-indene-2-carboxamido)acetic acid;
2-(5-(3-chlorophenyl)-3-hydroxy-1-oxo-1H-indene-2-carboxamido)acetic acid;
2-(5-cyclopropyl-3-hydroxy-1-oxo-1H-indene-2-carboxamido)acetic acid;
2-(3-hydroxy-1-oxo-5-(pyridin-3-yl)-1H-indene-2-carboxamido)acetic acid;
2-(3-hydroxy-1-oxo-5-(thiophen-2-yl)-1H-indene-2-carboxamido)acetic acid;
2-(3-hydroxy-1-oxo-4-(tetrahydro-2H-pyran-4-yl)-1H-indene-2-carboxamido)acetic acid;

2-(3-hydroxy-1-oxo-4-(pyridin-3-yl)-1H-indene-2-carboxamido)acetic acid; or 2-(3-hydroxy-1-oxo-4-(trifluoromethyl)-1H-indene-2-carboxamido)acetic acid.

Compounds of the present disclosure can contain one or more chiral centers. Such compounds can be prepared or isolated as pure stereoisomers, i.e., as individual enantiomers or diastereomers, or as stereoisomer-enriched mixtures. All such stereoisomers, and enriched mixtures thereof, are included within the scope of the present disclosure. Pure stereoisomers, and enriched mixtures thereof, can be prepared using, for example, optically active starting materials or stereoselective reagents well-known in the art. Alternatively, racemic mixtures of such compounds can be separated using, for example, chiral column chromatography, chiral resolving agents and the like.

In some embodiments, the at least one compound is a salt. Such salts may be anhydrous or associated with one or more molecules of water as a hydrate.

In some embodiments, the compound is a prodrug. In some such embodiments, the compound is a ($C_1$-$C_6$)alkyl ester such as a methyl, ethyl, propyl, butyl, pentyl, or hexyl ester.

Also provided herein are pharmaceutical compositions that include at least one pharmaceutically acceptable carrier, excipient, or diluent, and a therapeutically effective amount of at least one compound of any of the embodiments described herein. In such embodiments, the at least one compound is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

Further provided are pharmaceutical compositions that include at least one pharmaceutically acceptable carrier, and a therapeutically effective amount of at least one compound of any of the embodiments described herein in combination with at least one additional compound such as an erythropoiesis stimulating agent or a chemotherapeutic agent.

Additionally provided is a method of increasing or stabilizing HIF levels or activity in a subject by administering to the subject at least one compound of any of the embodiments described herein.

Further provided is a method of treating a condition where it is desired to modulate HIF activity comprising administering to a subject at least one compound of any of the embodiments described herein. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

Also provided is a method of treating a hypoxic or ischemic related disorder in a subject comprising administering to a subject at least one compound of any of the embodiments described herein.

Also provided is a method of treating anemia in a subject comprising administering to a subject at least one compound of any of the embodiments described herein.

Further provided is a method of modulating the amount of HIF in a cell comprising contacting the cell with at least one compound of any of the embodiments described herein.

The compounds of the invention may also be used to prepare medicaments or in methods for stimulating erythropoiesis in a subject. Such methods and medicaments utilize a compound of any of the embodiments of the invention. In such methods, a compound of any of the embodiments is typically administered to a subject such as a human subject in a therapeutically effective amount.

Additionally provided is a method of increasing the amount of hemoglobin F in a subject comprising administering to the subject at least one compound of any of the embodiments described herein.

Also provided is a method of modulating angiogenesis in a subject comprising administering to the subject at least one compound of any of the embodiments described herein.

Additionally provided is a method of treating at least one disease in a patient in need of such treatment comprising administering to the patient a therapeutically effective amount of at least one compound of any of the embodiments described herein. In some such embodiments, the at least one disease is selected from ischemia, anemia, wound healing, auto-transplantation, allo-transplantation, xeno-transplantation, systemic high blood pressure, thalassemia, diabetes, cancer, or an inflammatory disorder.

Also provided is a method of inhibiting HIF hydroxylation in a subject comprising administering to the subject at least one compound of any of the embodiments described herein.

In some embodiments, the HIF PHD inhibitory activity $IC_{50}$ value of the compound is 40 µM or less. In other embodiments, the HIF PHD inhibitory activity $IC_{50}$ value of the compound is 10 µM or less. In still other embodiments, the HIF PHD inhibitory activity $IC_{50}$ value of the compound is 100 nM or less, whereas in others it is 10 nM or less.

In some embodiments, the at least one compound of any of the embodiments is used in the preparation of a medicament.

In some such embodiments, the at least one compound of any of the embodiments is used in the preparation of a medicament for increasing or stabilizing HIF levels or activity in a subject.

In some such embodiments, the at least one compound of any of the embodiments is used in the preparation of a medicament for treating a condition where it is desired to modulate HIF activity. In some such embodiments, the condition is selected from at least one of ischemia, anemia, wound healing, auto-transplantation, allo-transplantation, xeno-transplantation, systemic high blood pressure, thalassemia, diabetes, cancer, or an inflammatory disorder.

In some embodiments, the at least one compound of any of the embodiments is used in the preparation of a medicament for treating a hypoxic or ischemic related disorder in a subject.

In some embodiments, the at least one compound of any of the embodiments is used in the preparation of a medicament for modulating the amount if HIF in a cell. In some embodiments, the at least one compound according to any of the embodiments is used to modulate the amount of HIF in a cell.

In some embodiments, the at least one compound of any of the embodiments is used in the preparation of a medicament for modulating angiogenesis in a subject.

In some embodiments, the at least one compound of any of the embodiments is used in the preparation of a medicament for inhibiting HIF hydroxylation in a subject.

In some embodiments, the at least one compound of any of the embodiments is used in the preparation of a medicament for treating anemia.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

Scheme 1 shows a general synthetic route that may be used to prepare the compounds of the invention. Further details of the synthetic route are provided in the Examples that follow.

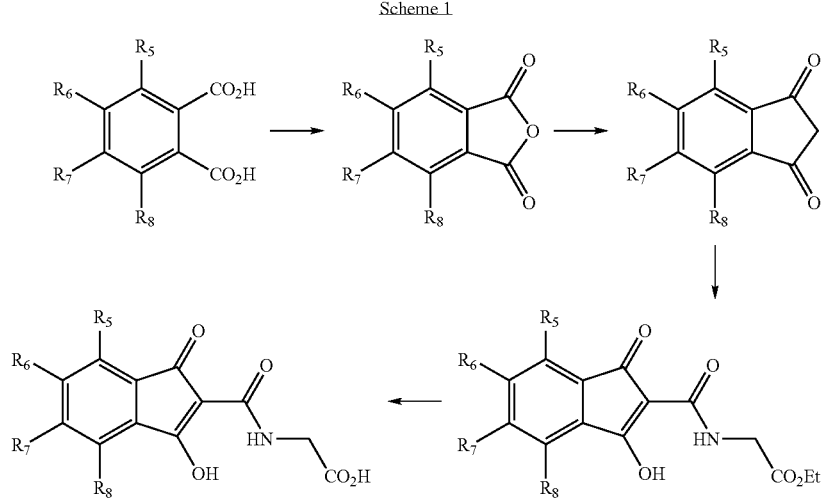

Scheme 1

The invention is further described by reference to the following examples, which are intended to exemplify the claimed invention but not to limit it in any way.

EXAMPLES

Unless otherwise stated, all compounds were obtained from commercial sources or were prepared using the methods and experimental procedures described herein. The following Abbreviations are used to refer to various reagents and solvents:
DCM Dichloromethane
DMSO Dimethylsulfoxide
EtOH Ethanol
MeOH Methanol
TEA Triethylamine
THF Tetrahydrofuran
TMS Trimethylsilyl
TR-FRET Time Resolved-Fluorescence Resonance Energy Transfer Method 1

Preparation of 2-(3-Hydroxy-4-iodo-1-oxo-1H-indene-2-carboxamido)acetic acid

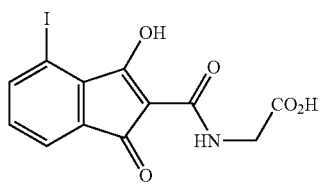

(a) 4-Iodoisobenzofuran-1,3-dione. A solution of 3-iodophthalic acid (5.00 g, 17 mmol, commercially available from Fluorchem Products, West Columbia, S.C.) and acetic anhydride (15 mL) was placed in a sealed flask and then heated in an oil bath at 140° C. for 4 hours. The solution was cooled to room temperature, and then placed in an ice bath. The solids were collected by filtration, washed with cold ether, and dried under vacuum.

(b) 4-Iodo-2H-indene-1,3-dione. To a stirred solution of 4-iodoisobenzofuran-1,3-dione (4.7 g, 17 mmol) and acetic anhydride (15 mL, 163 mmol) containing TEA (8.6 mL, 62 mmol) was added tert-butyl acetoacetate (3.1 mL, 19 mmol). After stirring for 6 hours at room temperature, the reaction was poured into a flask containing ice, and 5 N HCl (25 mL) was added dropwise. The resulting mixture was stirred for 5 minutes and then the flask was placed in an oil bath at 75° C. for 5 minutes. The flask was then cooled to room temperature, and the reaction was extracted several times with DCM (3×50 mL). The organic layers were combined, dried (sodium sulfate), filtered, and concentrated to provide a black oil.

(c) Ethyl 2-(3-hydroxy-4-iodo-1-oxo-1H-indene-2-carboxamido)acetate. To a stirred solution of 4-iodo-2H-indene-1,3-dione (1.70 g, 6.2 mmol) in THF (30 mL) was added 60% sodium hydride (0.25 g, 6.2 mmol). Once the vigorous gas evolution ceased, ethyl 2-isocyanatoacetate (0.71 mL, 6.2 mmol) was added to the purple reaction and stirring was continued for 1.5 hours. The THF was removed under reduced pressure, and then the solids were collected by filtration. Washing with cold ether provided pure title compound.

(d) 2-(3-Hydroxy-4-iodo-1-oxo-1H-indene-2carboxamido)acetic acid. To a solution of ethyl 2-(3-hydroxy-4-iodo-1-oxo-1H-indene-2-carboxamido)acetate in THF (25 mL) was added 5 N NaOH (30 mL). The reaction was stirred for 1 hour. The solids were filtered off and acidified with 5 N HCl. The yellow solid was filtered and then washed with water and cold ether. The resulting solid was dried in a vacuum oven overnight at 50° C. $^1$H NMR (400 MHz, DMSO-$d_6$) δ ppm 4.08 (s, 2H) 7.33 (t, J=7.43 Hz, 1H) 7.59 (d, J=7.24 Hz, 1H) 7.99 (d, J=7.83 Hz, 1H).

TABLE 1

The following table lists compounds which were prepared by the methods described above.

| Ex. | Structure | Name | $^1$H NMR DMSO-$d_6$ (δ ppm) | Method |
|---|---|---|---|---|
| 1 | 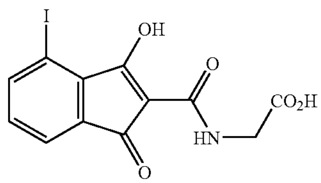 | 2-(3-hydroxy-4-iodo-1-oxo-1H-indene-2-carboxamido)acetic acid | 4.08(s, 2 H) 7.33(t, J = 7.43 Hz, 1 H) 7.59(d, J = 7.24 Hz, 1 H) 7.99(d, J = 7.83 Hz, 1 H) | 1 |
| 2 | 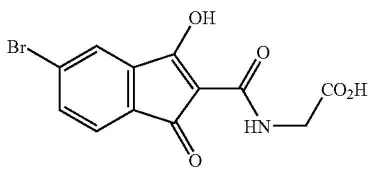 | 2-(5-bromo-3-hydroxy-1-oxo-1H-indene-2-carboxamido)acetic acid | 4.06(2 H, s), 7.48(1 H, d, J = 7.7 Hz), 7.65 (1 H, s), 7.79(1 H, d, J = 9.4 Hz) | 1(b)-(d) |
| 3 | 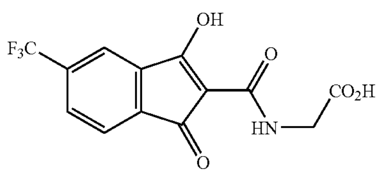 | 2-(3-hydroxy-1-oxo-5-(trifluoromethyl)-1H-indene-2-carboxamido)acetic acid | 4.07(s, 2 H) 7.69-7.78(m, 2 H) 7.93-8.01 (m, 1 H) | 1 |
| 4 | 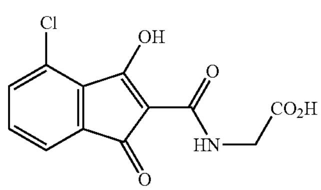 | 2-(4-chloro-3-hydroxy-1-oxo-1H-indene-2-carboxamido)acetic acid | 4.06(2 H, s), 7.49-7.53(1 H, m), 7.53-7.62 (2 H, m) | 1(b)-(d) |
| 5 | 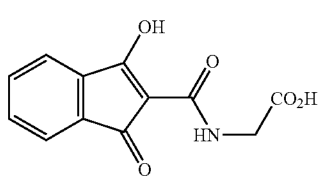 | 2-(3-hydroxy-1-oxo-1H-indene-2-carboxamido)acetic acid | 3.40(2 H, d, J = 4.1 Hz), 7.26 (2 H, dd, J = 5.0, 3.2 Hz), 7.37(2 H, dd, J = 4.8, 3.1 Hz), 8.60(1 H, t, J = 4.5 Hz) | 1(c)-(d) |
| 6 | 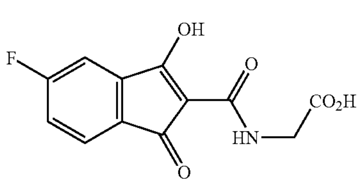 | 2-(6-fluoro-3-hydroxy-1-oxo-1H-indene-2-carboxamido)acetic acid | 8.90(br s, 1 H) 7.63(dd, J = 7.82, 4.89 Hz, 1 H) 7.32-7.49(m, 2 H) 4.09(s, 2 H) | 1 |

TABLE 1-continued

The following table lists compounds which were prepared by the methods described above.

| Ex. | Structure | Name | $^1$H NMR DMSO-$d_6$ (δ ppm) | Method |
|---|---|---|---|---|
| 7 | 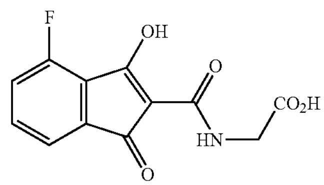 | 2-(7-fluoro-3-hydroxy-1-oxo-1H-indene-2-carboxamido)acetic acid | 8.89(br s, 1 H) 7.58-7.73(m, 1 H) 7.32-7.51 (m, 2 H) 4.07(s, 2 H) | 1 |
| 8 | 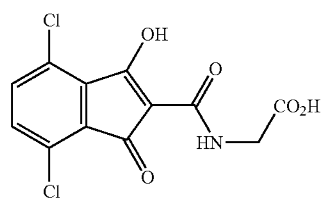 | 2-(4,7-dichloro-3-hydroxy-1-oxo-1H-indene-2-carboxamido)acetic acid | 9.01(br s, 1 H) 7.51(s, 2 H) 4.03(s, 2 H) | 1 |

Method 2

2-(3-Hydroxy-1-oxo-4-phenyl-1H-indene-2-carboxamido)acetic acid

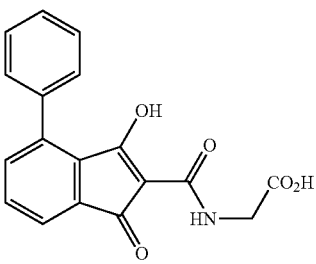

(a) Ethyl 2-(3-hydroxy-1-oxo-4-phenyl-1H-indene-2-carboxamido)acetate A 20 mL reaction tube was charged with ethyl 2-(3-hydroxy-4-iodo-1-oxo-1H-indene-2-carboxamido)acetate (120 mg, 0.30 mmol, Method 1), phenyl boronic acid (0.36 mmol, 1.2 eq, commercially available from Aldrich) and 4,5-bis(diphenylphosphino)-9,9-dimethylxanthene (11.6 mg, 0.02 mmol). A solution of sodium carbonate (79.5 mg, 0.75 mmol) in water (0.5 mL) was added, followed by a solution of palladium acetate (3.36 mg, 0.015 mmol) in degassed DMF (0.2 mL). Additional degassed DMF (1.2 mL) was then added, and the reaction vessel purged with nitrogen. The reaction vessel was capped and heated on a 95° C. shaker for 18 hours. The mixture was cooled to room temperature and filtered through Celite. The filtrate was purified by preparative HPLC.

(b) 2-(3-Hydroxy-1-oxo-4-phenyl-1H-indene-2-carboxamido)acetic acid. The title compound was prepared by saponification conditions analogous to Method 1(d).

Method 3

2-(3-hydroxy-1-oxo-6-phenyl-1H-indene-2-carboxamido)acetic acid

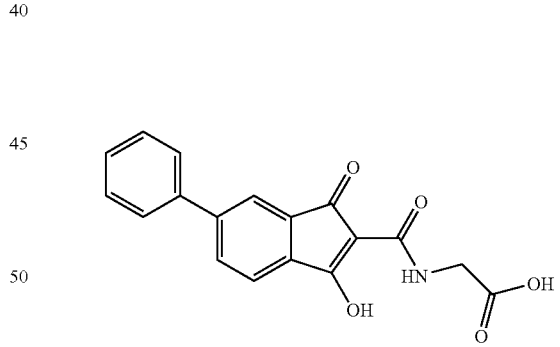

(a) ethyl 2-(3-hydroxy-1-oxo-6-phenyl-1H-indene-2-carboxamido)acetate. The title compound was prepared by a method analogous to Method 2(a) using ethyl 2-(6-bromo-3-hydroxy-1-oxo-1H-indene-2-carboxamido)acetate as starting material. Ethyl 2-(6-bromo-3-hydroxy-1-oxo-1H-indene-2-carboxamido)acetate was prepared by Method 1, as in Example 2.

(b) 2-(3-hydroxy-1-oxo-6-phenyl-1H-indene-2-carboxamido)acetic acid. The title compound was prepared analogously to Method 2(b).

TABLE 2

The following table lists compounds which were prepared by the methods 2 and 3 as described above.

| Ex. | Structure | Name | MS (M + H)+ | Method |
|---|---|---|---|---|
| 9 | 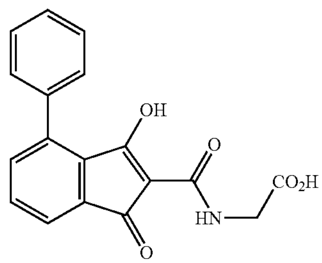 | 2-(3-hydroxy-1-oxo-7-phenyl-1H-indene-2-carboxamido)acetic acid | 324 | 2 |
| 10 | 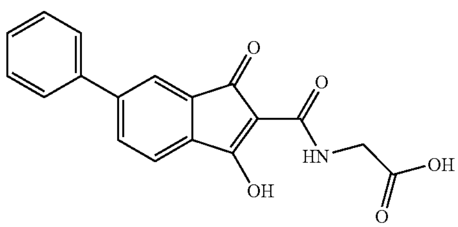 | 2-(3-hydroxy-1-oxo-6-phenyl-1H-indene-2-carboxamido)acetic acid | 324 | 3 |
| 11 | 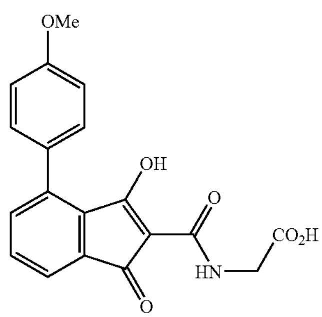 | 2-(3-hydroxy-4-(4-methoxyphenyl)-1-oxo-1H-indene-2-carboxamido)acetic acid | 353 | 2 |
| 12 | 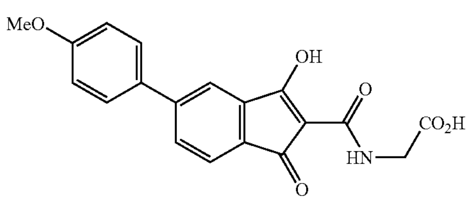 | 2-(3-hydroxy-5-(4-methoxyphenyl)-1-oxo-1H-indene-2-carboxamido)acetic acid | 353 | 3 |
| 13 | 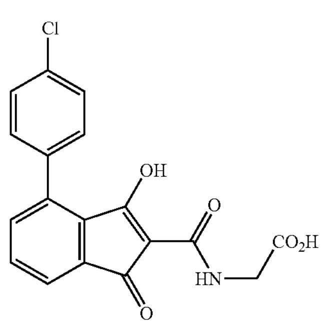 | 2-(4-(4-chlorophenyl)-3-hydroxy-1-oxo-1H-indene-2-carboxamido)acetic acid | 357 | 2 |

TABLE 2-continued

The following table lists compounds which were prepared by the methods 2 and 3 as described above.

| Ex. | Structure | Name | MS (M + H)+ | Method |
|---|---|---|---|---|
| 14 | 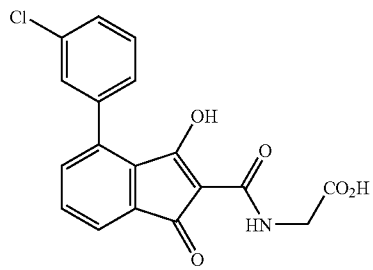 | 2-(4-(3-chlorophenyl)-3-hydroxy-1-oxo-1H-indene-2-carboxamido)acetic acid | 357 | 2 |
| 15 | 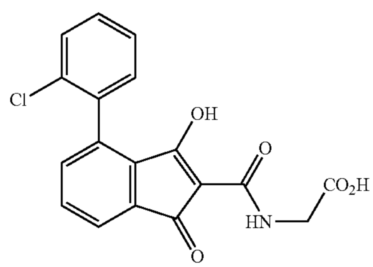 | 2-(4-(2-chlorophenyl)-3-hydroxy-1-oxo-1H-indene-2-carboxamido)acetic acid | 357 | 2 |
| 16 | 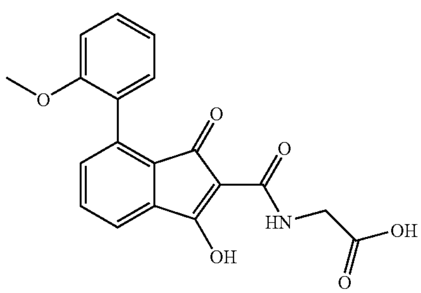 | 2-(3-hydroxy-7-(2-methoxyphenyl)-1-oxo-1H-indene-2-carboxamido)acetic acid | 353 | 2 |
| 17 | 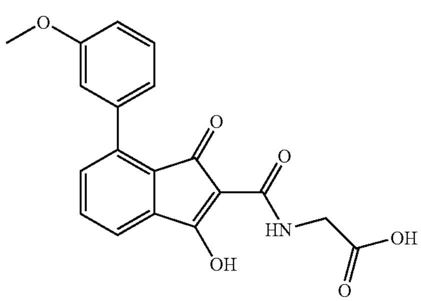 | 2-(3-hydroxy-7-(3-methoxyphenyl)-1-oxo-1H-indene-2-carboxamido)acetic acid | 353 | 2 |
| 18 | 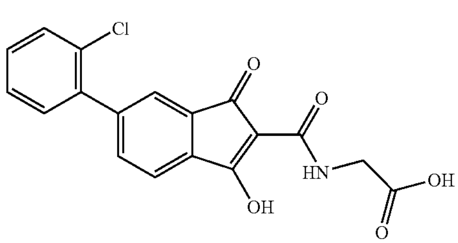 | 2-(6-(2-chlorophenyl)-3-hydroxy-1-oxo-1H-indene-2-carboxamido)acetic acid | 357 | 3 |

TABLE 2-continued

The following table lists compounds which were prepared by the methods 2 and 3 as described above.

| Ex. | Structure | Name | MS (M + H)+ | Method |
|---|---|---|---|---|
| 19 | 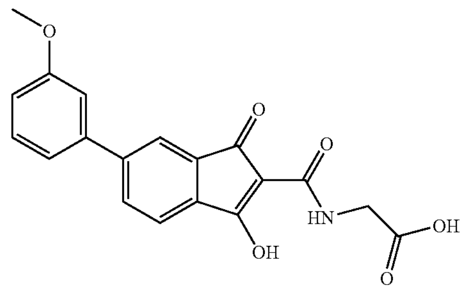 | 2-(3-hydroxy-6-(3-methoxyphenyl)-1-oxo-1H-indene-2-carboxamido)acetic acid | 353 | 3 |

Method 4

Preparation of 2-((Carboxymethyl)carbamoyl)-3-hydroxy-1-oxo-1H-indene-4-carboxylic acid

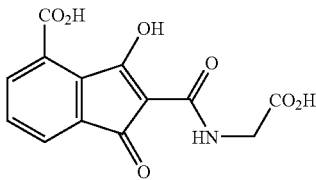

(a) Methyl 2-((2-ethoxy-2-oxoethyl)carbamoyl)-3-hydroxy-1-oxo-1H-indene-4-carboxylate. The title compound is prepared by metal mediated carbonylation of ethyl 2-(3-hydroxy-4-iodo-1-oxo-1H-indene-2-carboxamido)acetate with carbon monoxide in MeOH according to literature procedures.

(b) 2-((Carboxymethyl)carbamoyl)-3-hydroxy-1-oxo-1H-indene-4-carboxylic acid. The title compound is prepared by saponification conditions analogous to Method 1(d).

TABLE 3

The following table lists compounds which are prepared by the methods described above.

| Ex | Structure | Name | MW | Method |
|---|---|---|---|---|
| 20 | 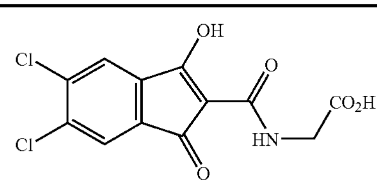 | 2-(5,6-dichloro-3-hydroxy-1-oxo-1H-indene-2-carboxamido)acetic acid | 316 | 1 |
| 21 | 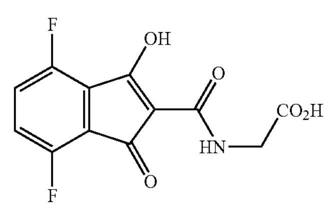 | 2-(4,7-difluoro-3-hydroxy-1-oxo-1H-indene-2-carboxamido)acetic acid | 283 | 1 |
| 22 | 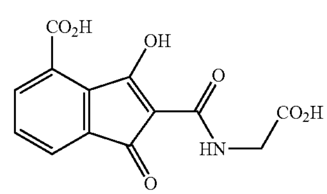 | 2-((carboxymethyl)carbamoyl)-3-hydroxy-1-oxo-1H-indene-4-carboxylic acid | 291 | 1, 4 |

TABLE 3-continued

The following table lists compounds which are prepared by the methods described above.

| Ex | Structure | Name | MW | Method |
|---|---|---|---|---|
| 23 | 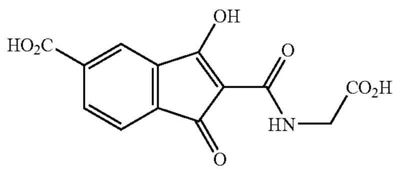 | 2-((carboxymethyl)carbamoyl)-3-hydroxy-1-oxo-1H-indene-5-carboxylic acid | 291 | 1, 4 |
| 24 | 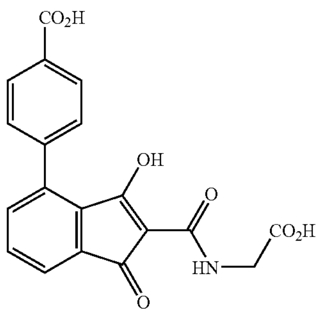 | 4-(2-((carboxymethyl)carbamoyl)-3-hydroxy-1-oxo-1H-inden-4-yl)benzoic acid | 367 | 1, 2 |
| 25 | 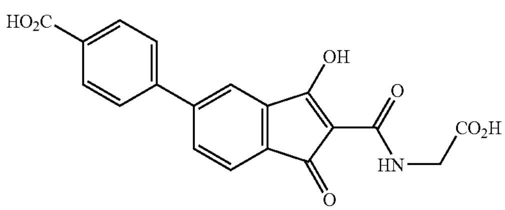 | 4-(2-((carboxymethyl)carbamoyl)-3-hydroxy-1-oxo-1H-inden-5-yl)benzoic acid | 367 | 1, 3 |
| 26 | 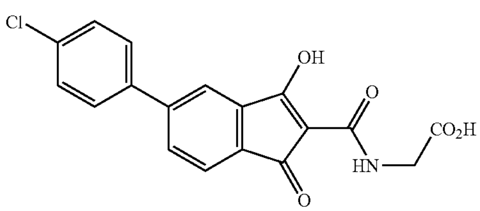 | 2-(5-(4-chlorophenyl)-3-hydroxy-1-oxo-1H-indene-2-carboxamido)acetic acid | 357 | 1, 3 |
| 27 | 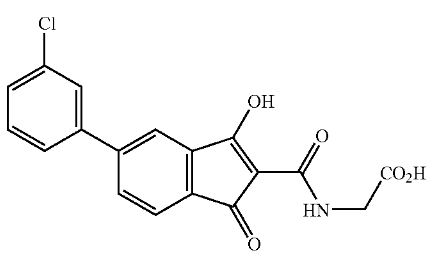 | 2-(5-(3-chlorophenyl)-3-hydroxy-1-oxo-1H-indene-2-carboxamido)acetic acid | 357 | 1, 3 |
| 28 | 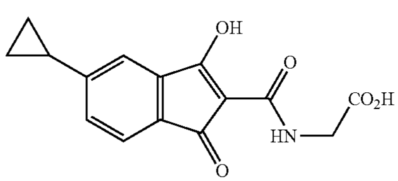 | 2-(5-cyclopropyl-3-hydroxy-1-oxo-1H-indene-2-carboxamido)acetic acid | 287 | 1, 3 |

TABLE 3-continued

The following table lists compounds which are prepared by the methods described above.

| Ex | Structure | Name | MW | Method |
|----|-----------|------|-----|--------|
| 29 | 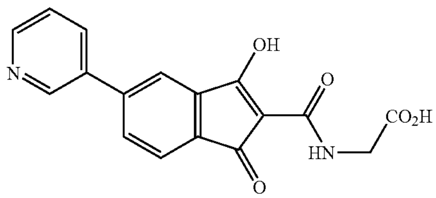 | 2-(3-hydroxy-1-oxo-5-(pyridin-3-yl)-1H-indene-2-carboxamido)acetic acid | 324 | 1, 3 |
| 30 | 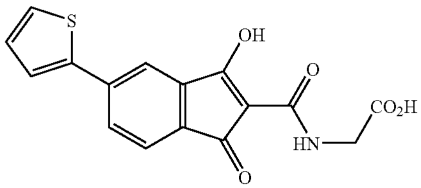 | 2-(3-hydroxy-1-oxo-5-(thiophen-2-yl)-1H-indene-2-carboxamido)acetic acid | 329 | 1, 3 |
| 31 | 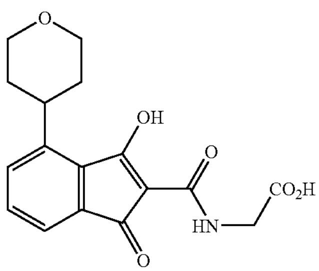 | 2-(3-hydroxy-1-oxo-4-(tetrahydro-2H-pyran-4-yl)-1H-indene-2-carboxamido)acetic acid | 331 | 1, 2 |
| 32 | 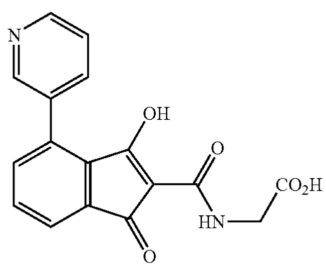 | 2-(3-hydroxy-1-oxo-4-(pyridin-3-yl)-1H-indene-2-carboxamido)acetic acid | 324 | 1, 2 |
| 33 | 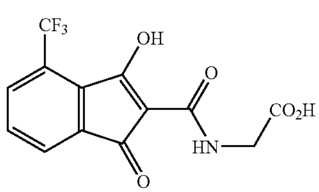 | 2-(3-hydroxy-1-oxo-4-(trifluoromethyl)-1H-indene-2-carboxamido)acetic acid | 315 | 1 |

The following are examples of methods that may be used to quantitate HIF PHD activity and the inhibition of HIF PHD activity by compounds of the present invention.

Expression, Purification and Europium Labeling of VCB and Design of an Eu-VCB Based TR-FRET Assay for the Detection of Hydroxyprolyl HIF1α Peptides The VCB complex is defined as the Von Hippel-Lindau protein (pVHL), elongin B and elongin C heterotrimeric complex. VCB specifically binds to hydroxyproline residues of HIF1α, initiating polyubiquitinylation of HIF1α and its subsequent proteolytic destruction. In the absence of prolyl hydroxylase activity, VCB does not bind unmodified HIF1α. The VCB complex was expressed in E. coli and purified from the soluble fraction. The amino acid sequences of the three protein components are as follows:

```
VHL (Amino Acids 54-213)
                                            (SEQ ID NO: 1)
MHHHHHHEAGRPRPVLRSVNSREPSQVIFCNRSPRVVLPVWLNFDGEPQP

YPTLPPGTGRRIHSYRGHLWLFRDAGTHDGLLVNQTELFVPSLNVDGQPI
```

```
                        -continued
FANITLPVYTLKERCLQVVRSLVKPENYRRLDIVRSLYEDLEDHPNVQKD

LERLTQERIAHQRMGD

ElonginB
                                            (SEQ ID NO: 2)
MDVFLMIRRHKTTIFTDAKESSTVFELKRIVEGILKRPPDEQRLYKDDQL

LDDGKTLGECGFTSQTARPQAPATVGLAFRADDTFEALCIEPFSSPPELP

DVMKPQDSGSSANEQAVQ*

ElonginC (Amino Acids 17-112)
                                            (SEQ ID NO: 3)
MYVKLISSDGHEFIVKREHALTSGTIKAMLSGPGQFAENETNEVNFREIP

SHVLSKVCMYFTYKVRYTNSSTEIPEFPIAPEIALELLMAANFLDC
```

The N-terminus of VHL contains a six histidine affinity tag for purification purposes.

A VCB-based assay allows a highly sensitive and direct measurement of enzymatic product formation (HIF1α protein or fragments thereof containing a hydroxylated proline residue) and is suitable for high throughput screening.

For expression in *E. coli*, VHL 54-213 was cloned into pAMG21 (Plux promoter) between the NdeI-XhoI site. Immediately downstream of this is the ElonginC gene cloned into the XhoI site to SacII. There is a 13 bp spacer between the stop codon of VHL and the initiating codon of ElonginC. The expression plasmid pAMG21 is a 6118 base pair plasmid that was derived from the expression vector pCFM1656 (ATCC #69576), which in turn can be derived from the expression vector system described in U.S. Pat. No. 4,710,473. This design allows for chemical rather than thermal induction of protein expression by substitution of the promoter region, replacing a synthetic bacteriophage lambda pl promoter with a DNA segment containing the LuxR gene and the LuxPR promoter, and affords regulation of expression by the plasmid-encoded LuxR protein, thereby allowing any *E. coli* strain to serve as host.

ElonginB was cloned into pTA2 (pACYC184.1 based vector) under the control of a Lac promoter. Competent *E. coli* cells were transformed with the pAMG21-VHL-ElonginC construct. These *E. coli* cells were rendered competent again prior to transformation with the pTA2-elonginB construct to produce the final *E. coli* strain containing both plasmid constructs. Induction of protein expression was initiated by the addition of IPTG and N-(3-oxo-hexanoyl)-homoserine lactone (HSL) at 30° C.

Bacterial cells were lysed by a microfluidizer in aqueous buffer of pH 8.0 and the soluble fraction was separated by centrifugation. The soluble *E. coli* fraction was subjected to Nickel-NTA chelating chromatography to utilize the six histidine affinity tag located on the pVHL construct. The pooled fractions from the nickel column were applied to a Superdex 200 size exclusion chromatography (SEC) column. The protein eluted as a monomer on SEC, indicating that the three protein components formed a complex in solution. The fractions from the SEC column were pooled and applied to a Q Sepharose anion exchange column for final purification. The purified complex was visualized by SDS-PAGE and the identities of the three protein components were confirmed by N-terminal amino acid sequencing.

Purified VCB was exchanged into 50 mM sodium carbonate buffer pH 9.2 and labeled with a europium chelate overnight. LANCE™ europium chelate (PerkinElmer, Inc; Eu-W1024 ITC chelate; catalog number is AD0013) was used to label the lysine residues of the VCB complex. The chelate contains an isothiocyanate reactive group that specifically labels proteins on lysine residues (there are fifteen lysine residues in the VCB protein complex). The resulting europylated VCB was purified by desalting columns and quantitated by standard means. The labeling yield was determined to be 6.6 europium groups per one VCB complex.

Two peptides were produced by SynPep, Inc.: a hydroxyproline modified peptide and an unmodified control peptide. VCB was expected to specifically bind to the hydroxyproline modified peptide (a mimic of enzymatic hydroxylation by prolyl hydroxylase). VCB was not expected to bind to the unmodified peptide. Both peptides were produced with a biotin group at the N-terminus to allow for binding by the streptavidin-labeled fluorescent acceptor allophycocyanin (streptavidin APC; Prozyme, Inc.).

The sequence of the custom synthesized HIF1α peptides (amino acids 556-575, with methionine residues replaced with alanine residues to prevent oxidation) were as follows:

```
                                                    (SEQ ID NO: 4)
(unmodified)  Biotin-DLDLEALAPYIPADDDFQLR-CONH₂

(SEQ ID NO: 5)
(modified)    Biotin-DLDLEALA[hyP]YIPADDDFQLR-CONH₂
```

The peptides were purchased from SynPep as lyophilized solids and were suspended in DMSO for experimental use. The peptides were quantitated according to their absorbance at 280 nm.

Experiments were conducted in 96 well Costar polystyrene plates. Biotinylated peptides and europylated VCB were suspended in the following buffer: 100 mM HEPES 7.5, 0.1 M NaCl, 0.1% BSA and 0.05% Tween 20. The reagents were allowed to reach equilibrium by shaking for 1 hour before the plates were read on the Discovery Instrument (Packard). The data output is the ratio of the 665 nm and 620 nm emission signal resulting from the 320 nm excitation.

As shown in FIG. 1, the specific interaction of europylated VCB with the hydroxyproline modified HIF1α peptide coupled to streptavidin APC generated a fluorescence signal detectable over the background signal. These results demonstrate a fluorescence signal generated by the specific interaction of Eu-VCB with hyp-HIF1α peptide. Each bar represents the data from a single well of a 96 well assay plate. The signal to background ratio was calculated from data from a control plate (unmodified peptide). Eu-VCB concentration was titrated across rows (nM) and streptavidin APC concentrations were titrated down columns. The peptide concentration was fixed at 100 nM.

Detection of Enzymatically Converted Hydroxyprolyl HIF-1α by HIF PHD2 and Inhibition of HIF PHD2 Activity Binding of the P564-HIF1α peptide to VCB was validated utilizing the homogeneous time-resolved FRET (TR-FRET) technology. A 17 amino acid (17aa) peptide with an N-terminally labeled biotin molecule corresponding to amino acid sequences 558 to 574 of the HIF1α protein was synthesized in-house (DLEMLAPYIPMDDDFQL (SEQ ID NO: 6)). A second 17aa peptide containing a hydroxylated proline at position 564 was chemically generated to mimic the PHD enzyme converted product form of the protein that is recognized by VCB. The assay was performed in a final volume of 100 μL in buffer containing 50 mM Tris-HCl (pH 8), 100 mM NaCl, 0.05% heat inactivated FBS, 0.05% Tween-20, and 0.5% NaN₃. The optimal signal over background and the linear range of detection was determined by titrating the hydroxylated or unhydroxylated peptide at varied concentrations between 0 and 1 µM with a titration of VCB-Eu at varying concentrations between 0 and 50 nM with 50 nM of streptavidin APC. The binding reagents were allowed to reach equilibrium by shaking for 1 hour before it was read on the Discovery Instrument (Packard). The data output is the ratio of the 665 nm and 620 nm emission signal resulting from the 320 nm excitation.

HIF PHD2 activity was detected by P564-HIF1α peptide and VCB binding in the TR-FRET format. HIF PHD2 was assayed at various concentrations between 0 and 400 nM with 3 µM HIF1α peptide in buffer containing 50 mM Tris-HCl (pH 7.5), 100 mM NaCl, 0.05% Tween 20, 2 mM 2-oxoglutarate (2-OG), 2 mM ascorbic acid and 100 µM $FeCl_2$ in a final volume of 100 µL. The time-course was determined by periodically transferring 2.5 µL of the reaction into 250 µL of 10×TR-FRET buffer containing 500 mM HEPES (pH 7.5), 1 M NaCl, 1% BSA, and 0.5% Tween-20 to terminate the enzyme reaction. 15 nM HIF-1α peptide from the terminated reaction was added to 35 nM streptavidin-APC and 10 nM VCB-Eu to a final volume of 100 µL in 10×TR-FRET buffer. The TR-FRET reagents were placed on a shaker for 1 hour before detection on the Discovery platform.

Figure 2A:
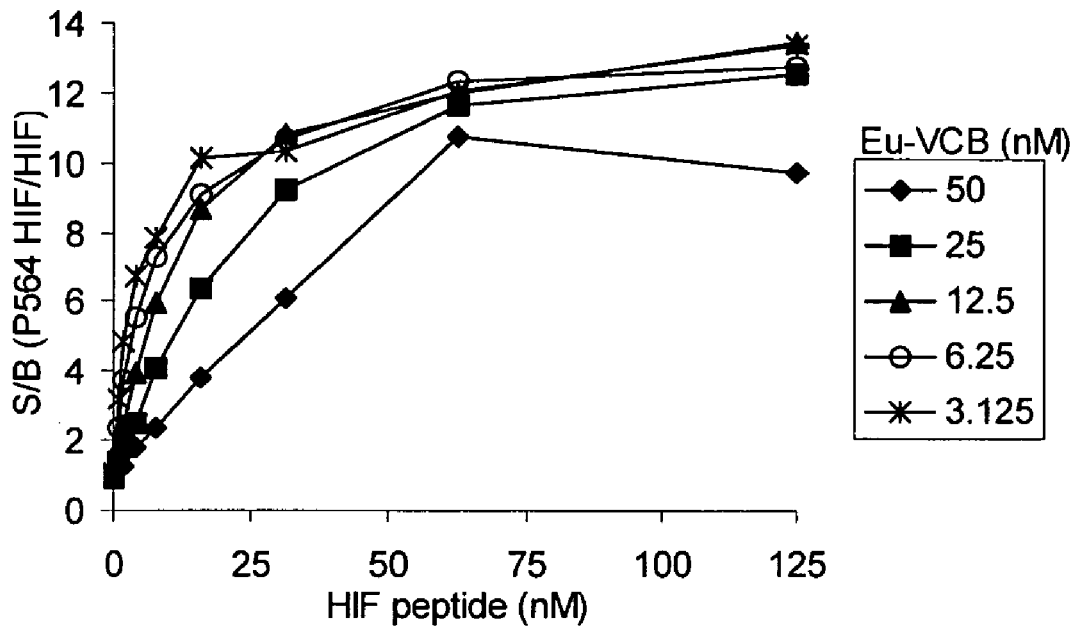
FIGS. 2A and 2B are graphs illustrating the ratio of TR-FRET signal generated by the interaction of Eu-VCB with streptavidin-APC-hydroxyprolyl HIF1α peptide over background signal generated by the interaction of Eu-VCB with streptavidin-APC-HIF1α peptide (nonhydroxylated).
Figure 2B:
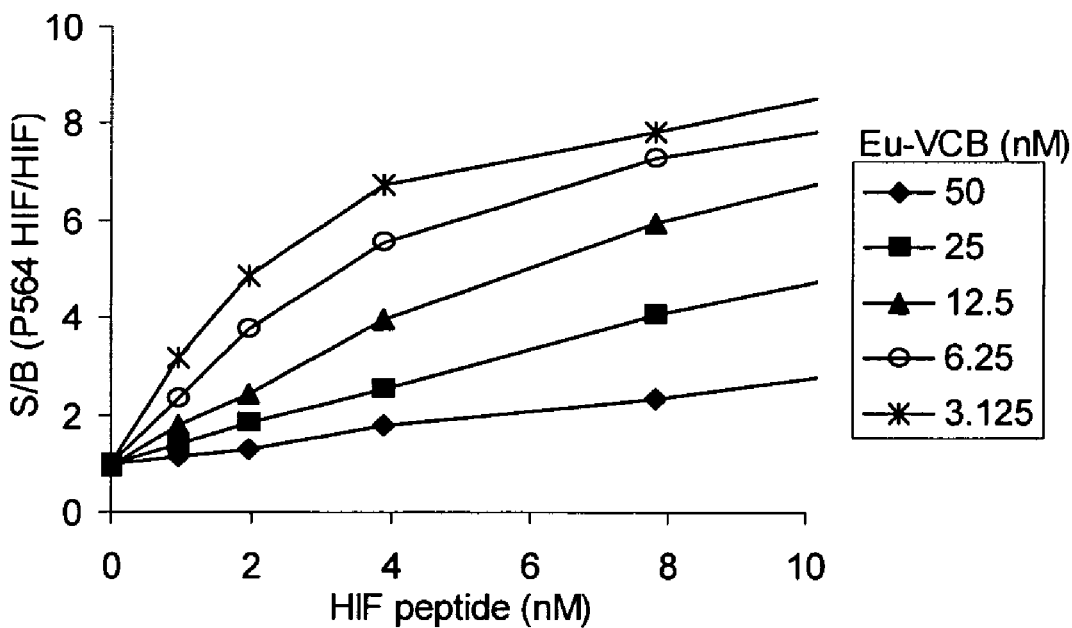

As demonstrated in FIGS. 2A and 2B, there was a dose dependent increase in TR-FRET signal resulting from binding of the hydroxylated-P564-HIF1α peptide to VCB-Eu compared to the unhydroxylated form of the peptide resulting in a 14 fold signal over noise ratio at 125 nM HIF1α peptide. VCB binding to the APC bound peptide permits a FRET transfer between the Eu and APC. The signal was linear to 2 nM peptide with 3.125 nM VCB, but increases to 62.5 nM peptide with 50 nM VCB resulting in a larger linear range.

Figure 3A:
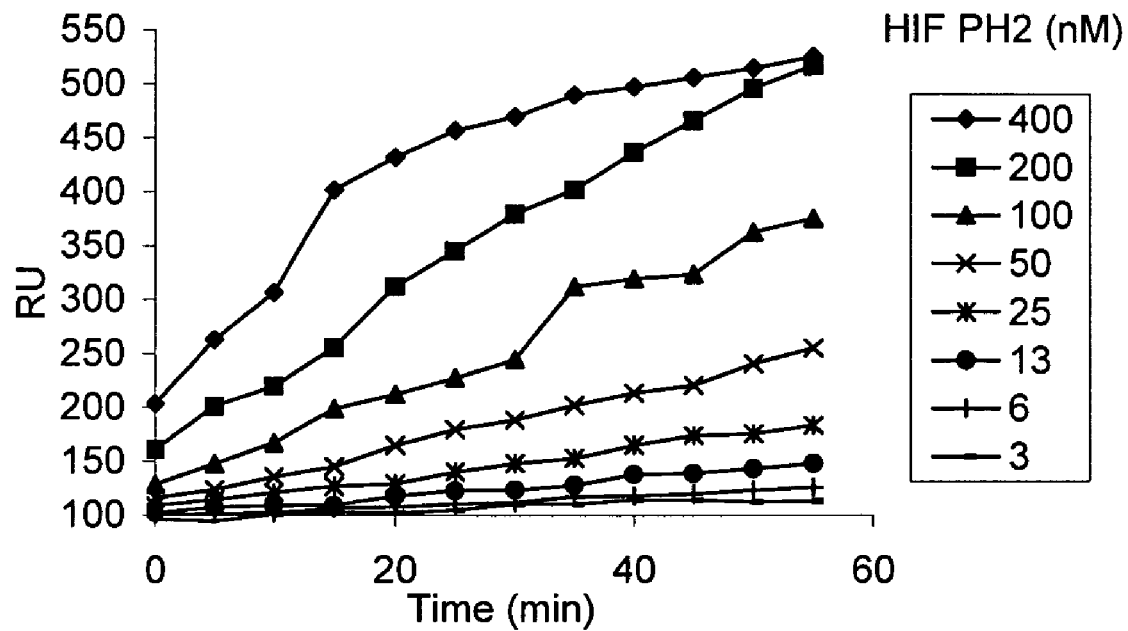
FIGS. 3A and 3B are graphs illustrating VCB binding and TR-FRET detection for determining HIF PHD2 hydroxylation of a HIF1α peptide.
Figure 3B:
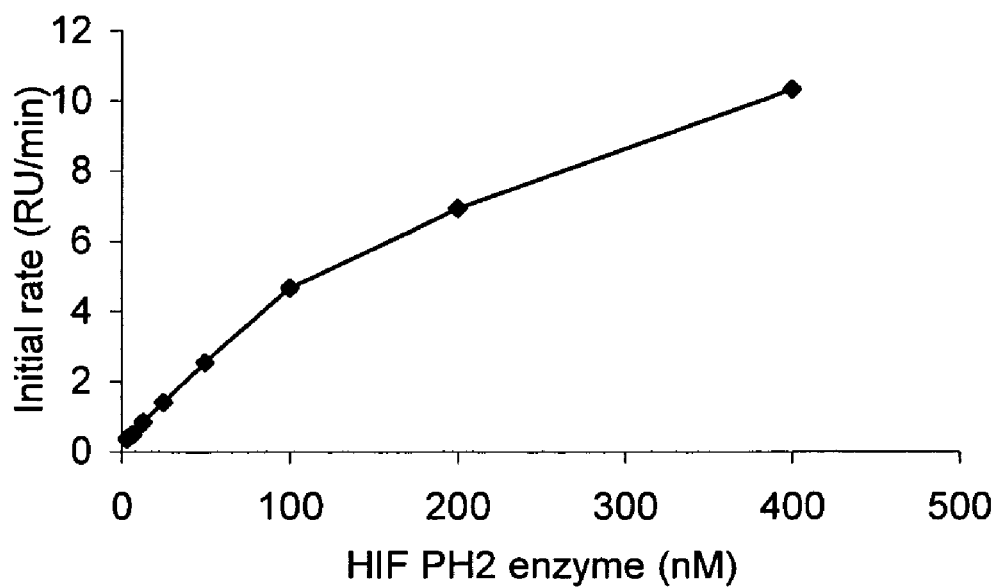

TR-FRET detection utilizing Eu-labeled VCB is a practical system for determining HIF PHD2 catalytic activity. HIF PHD2 hydroxylation of the HIF1α peptide results in the increase affinity of VCB to the peptide and hence and increased FRET signal. As shown in FIGS. 3A and 3B, activity was verified with a fairly linear and an increasing TR-FRET signal over time. There was a dose dependant increase in initial rates with increasing HIF PHD2 enzyme concentration up to 400 nM. The initial rates were linear to 100 nM enzyme.

Inhibition of HIF PHD2 activity was quantified utilizing the TR-FRET technology. HIF PHD2 catalyzes a hydroxyl modification on the proline residue of the P564-HIF1α peptide substrate (Biotin-DLEMLAPYIPMDDDFQL (SEQ ID NO: 7)) resulting in recognition and binding of the europylated Von Hippel-Lindau protein (pVHL), elongin B and elongin C heterotrimeric (VCB-Eu) complex.

The PHD2 inhibition assay was executed by addition of freshly dissolved $FeCl_2$ to 178.57 µM (100 µM final concentration) in PHD2 Reaction Buffer containing 30 mM MES, pH 6, 10 mM NaCl, 0.25% Brij-35, 0.01% BSA, and 1% DMSO. 28 µL of the iron solution and 2 µL of inhibitor compounds serially diluted in 100% DMSO (5% DMSO final) were added to black polypropylene 96-well microtiter plates. To that, 10 µL of 10 nM PHD2 (2 nM final) was added to all wells of the plate except for the 8 wells of column 12 (LO control), and allowed to incubate at room temperature on the shaker for one hour. Column 6 was the HI control containing PHD2 enzyme and 5% DMSO vehicle, but no inhibitor compound. To initiate the PHD2 enzymatic reaction, 10 µL of a solution containing 500 nM P564-HIF1α peptide (100 nM final), 10 mM ascorbic acid (2 mM final), and 1.25 µM 2-oxoglutarate (α-ketoglutarate; 0.25 µM final) in PHD2 Reaction Buffer was added to all wells of the plate and allowed to incubate on the shaker at room temperature for one hour.

The reaction was terminated by addition of 25 µL TR-FRET Buffer (50 mM TRIS-HCl, pH 9, 100 mM NaCl, 0.05% BSA, and 0.5% Tween-20) containing 150 mM succinate (product inhibitor; 50 mM final), 75 nM streptavidin-APC (25 nM final), and 7.5 nM VCB-Eu (2.5 nM final). The TR-FRET detection reagents were placed on a shaker for 1 hour to reach binding equilibrium before reading on the Discovery platform (PerkinElmer). Europium is excited at 315 nm and phosphoresces at 615 nm with a large Stoke's shift. APC, in turn, emits at 655 nm upon excitation at 615 nm. The TR-FRET signal is measured as the ratio of the APC 655 nm signal divided by the internal europium reference 615 nm emission signal.

The POC (percentage of control) was determined by comparing the signal from hydroxylated peptide substrate in the enzyme reaction containing inhibitor compound with that from PHD2 enzyme with DMSO vehicle alone (HI control), and no enzyme (LO control). POC was calculated using the formula: % control (POC)=(cpd−average LO)/(average HI−average LO)*100. Data (consisting of POC and inhibitor concentration in µM) was fitted to a 4-parameter equation (y=A+((B−A)/(1+((x/C)^D))), where A is the minimum y (POC) value, B is the maximum y (POC), C is the x (cpd concentration) at the point of inflection and D is the slope factor) using a Levenburg-Marquardt non-linear regression algorithm.

In certain embodiments, compounds of the present invention exhibit a HIF PHD inhibitory activity $IC_{50}$ value of 40 µM or less. In additional embodiments, compounds of the present invention exhibit a HIF PHD inhibitory activity $IC_{50}$ value of 10 µM or less and in further embodiments, compounds of the present invention exhibit a HIP PHD inhibitory activity $IC_{50}$ value of 5 µM or less.

The following table includes PHD2 $IC_{50}$ values obtained using the procedures set forth herein for various Examples compounds described herein.

| Table of PHD2 $IC_{50}$ values of Example Compounds | | |
|---|---|---|
| Example | Structure | PHD2 $IC_{50}$ (µM) |
| 1 | (structure) | 0.0225 |
| 2 | (structure) | 0.0206 |

Table of PHD2 IC$_{50}$ values of Example Compounds

| Example | Structure | PHD2 IC$_{50}$ (μM) |
|---|---|---|
| 3 | 5-CF$_3$ indanone-2-carboxamide-glycine | 0.0130 |
| 4 | 4-Cl indanone-2-carboxamide-glycine | 0.0095 |
| 6 | 5-F indanone-2-carboxamide-glycine | 0.0501 |
| 7 | 4-F indanone-2-carboxamide-glycine | 0.0255 |
| 8 | 4,7-diCl indanone-2-carboxamide-glycine | 0.0472 |
| 9 | 4-phenyl indanone-2-carboxamide-glycine | 0.0028 |
| 10 | 5-phenyl indanone-2-carboxamide-glycine | 0.0116 |
| 11 | 4-(4-methoxyphenyl) indanone-2-carboxamide-glycine | 0.0036 |
| 12 | 5-(4-methoxyphenyl) indanone-2-carboxamide-glycine | 0.0220 |
| 13 | 4-(4-chlorophenyl) indanone-2-carboxamide-glycine | 0.0038 |
| 14 | 4-(3-chlorophenyl) indanone-2-carboxamide-glycine | 0.0030 |
| 15 | 4-(2-chlorophenyl) indanone-2-carboxamide-glycine | 0.0085 |

Table of PHD2 IC$_{50}$ values of Example Compounds

| Example | Structure | PHD2 IC$_{50}$ (μM) |
|---|---|---|
| 16 | 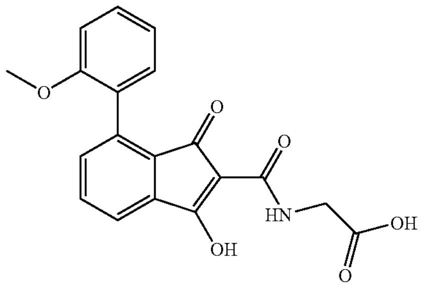 | 0.0221 |
| 17 | 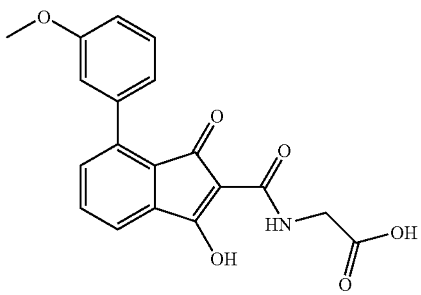 | 0.0030 |
| 18 | 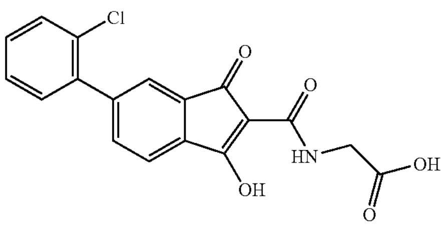 | 0.0036 |
| 19 | | 0.0055 |

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. At least one compound of Formula I:

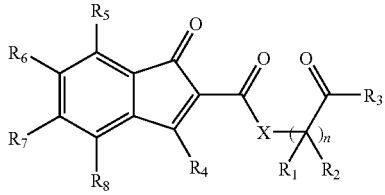

a pharmaceutically acceptable salt thereof, a tautomer thereof, or a pharmaceutically acceptable salt of the tautomer; a chelate thereof, a non-covalent complex thereof, or a mixture of any of the foregoing, wherein:

n is 1 to 6;

X is —$NR_a$—, wherein $R_a$ is H;

each instance of $R_1$ and $R_2$ is independently selected from H, lower alkyl, substituted lower alkyl, lower haloalkyl, or substituted lower haloalkyl, or $R_1$ and $R_2$, together with the carbon to which they are attached, can join to form a 3-6 membered optionally substituted ring comprising 0, 1, or 2 heteroatoms selected from O, N, and S;

$R_3$ is selected from OH, SH, $NH_2$, lower alkyl, substituted lower alkyl, lower alkoxy, substituted lower alkoxy, or sulfanyl;

$R_4$ is OH;

$R_5$, $R_6$, $R_7$, and $R_8$ are independently selected from H, Cl, F, Br, I, alkyl, substituted alkyl, alkenyl, substituted alkenyl, alkynyl, substituted alkynyl, $NR_bR_c$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, haloalkyl, perhaloalkyl, or —Y—$R_{10}$, wherein:

Y is selected from —$N(R_{11})$—Z— or —Z—$N(R_{11})$—;

Z is selected from C(O), $SO_2$, alkylene, substituted alkylene, alkenylene, substituted alkenylene, alkynylene, or substituted alkynylene;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl or substituted heteroaryl;

$R_{11}$ is selected from H, lower alkyl, or substituted lower alkyl; and $R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring, wherein, the compound is other than 2-(3-hydroxy-1-oxo-1H-indene-2-carboxamido)acetic acid or a methyl, ethyl, or propyl ester thereof.

2. The at least one compound according to claim 1, wherein $R_3$ is OH.

3. The at least one compound according to claim 1, wherein at least one instance of $R_5$, $R_6$, $R_7$, or $R_8$ is a substituted or unsubstituted aryl, a substituted or unsubstituted heteroaryl, a substituted or unsubstituted cycloalkyl, or a substituted or unsubstituted heterocyclyl group.

4. The at least one compound according to claim 3, wherein at least one instance of $R_5$, $R_6$, $R_7$, or $R_8$ is a phenyl or substituted phenyl group.

5. The at least one compound according to claim 1, wherein at least one instance of $R_5$, $R_6$, $R_7$, or $R_8$ is chosen from a halo or a moiety substituted with at least one halo.

6. The at least one compound according claim 5, wherein at least one instance of $R_5$, $R_6$, $R_7$, or $R_8$ is $CF_3$.

7. The at least one compound according to claim 1, wherein n is 1.

8. The at least one compound according to claim 1, wherein n is 1 and $R_3$ is OH or a salt thereof.

9. The at least one compound according to claim 1, wherein $R_1$ and $R_2$ are independently selected from H and lower alkyl.

10. The at least one compound according to claim 9, wherein $R_1$ and $R_2$ are independently selected from H and methyl.

11. The at least one compound according to claim 10, wherein $R_1$ and $R_2$ are both H.

12. The at least one compound according to claim 1, wherein the compound is selected from one of the following compounds or is a salt thereof, a tautomer thereof, or a salt of the tautomer:

2-(3-hydroxy-4-iodo-1-oxo-1H-indene-2-carboxamido) acetic acid;

2-(5-bromo-3-hydroxy-1-oxo-1H-indene-2-carboxamido)acetic acid;

2-(3-hydroxy-1-oxo-5-(trifluoromethyl)-1H-indene-2-carboxamido)acetic acid;

2-(4-chloro-3-hydroxy-1-oxo-1H-indene-2-carboxamido) acetic acid;

2-(6-fluoro-3-hydroxy-1-oxo-1H-indene-2-carboxamido) acetic acid;

2-(7-fluoro-3-hydroxy-1-oxo-1H-indene-2-carboxamido) acetic acid;

2-(4,7-dichloro-3-hydroxy-1-oxo-1H-indene-2-carboxamido)acetic acid;

2-(3-hydroxy-1-oxo-7-phenyl-1H-indene-2-carboxamido)acetic acid;

2-(3-hydroxy-1-oxo-6-phenyl-1H-indene-2-carboxamido)acetic acid;

2-(3-hydroxy-4-(4-methoxyphenyl)-1-oxo-1H-indene-2-carboxamido)acetic acid;

2-(3-hydroxy-5-(4-methoxyphenyl)-1-oxo-1H-indene-2-carboxamido)acetic acid;

2-(4-(4-chlorophenyl)-3-hydroxy-1-oxo-1H-indene-2-carboxamido)acetic acid;

2-(4-(3-chlorophenyl)-3-hydroxy-1-oxo-1H-indene-2-carboxamido)acetic acid;

2-(4-(2-chlorophenyl)-3-hydroxy-1-oxo-1H-indene-2-carboxamido)acetic acid;

2-(3-hydroxy-7-(2-methoxyphenyl)-1-oxo-1H-indene-2-carboxamido)acetic acid;

2-(3-hydroxy-7-(3-methoxyphenyl)-1-oxo-1H-indene-2-carboxamido)acetic acid;

2-(6-(2-chlorophenyl)-3-hydroxy-1-oxo-1H-indene-2-carboxamido)acetic acid;

or 2-(3-hydroxy-6-(3-methoxyphenyl)-1-oxo-1H-indene-2-carboxamido)acetic acid.

13. The at least one compound according to claim 1, wherein the compound is selected from one of the following compounds or is a salt thereof, a tautomer thereof, or a salt of the tautomer:

2-(5,6-dichloro-3-hydroxy-1-oxo-1H-indene-2-carboxamido)acetic acid;

2-(4,7-difluoro-3-hydroxy-1-oxo-1H-indene-2-carboxamido)acetic acid;
2-((carboxymethyl)carbamoyl)-3-hydroxy-1-oxo-1H-indene-4-carboxylic acid;
2-((carboxymethyl)carbamoyl)-3-hydroxy-1-oxo-1H-indene-5-carboxylic acid;
4-(2-((carboxymethyl)carbamoyl)-3-hydroxy-1-oxo-1H-inden-4-yl)benzoic acid;
4-(2-((carboxymethyl)carbamoyl)-3-hydroxy-1-oxo-1H-inden-5-yl)benzoic acid;
2-(5-(4-chlorophenyl)-3-hydroxy-1-oxo-1H-indene-2-carboxamido)acetic acid;
2-(5-(3-chlorophenyl)-3-hydroxy-1-oxo-1H-indene-2-carboxamido)acetic acid;
2-(5-cyclopropyl-3-hydroxy-1-oxo-1H-indene-2-carboxamido)acetic acid;
2-(3-hydroxy-1-oxo-5-(pyridin-3-yl)-1H-indene-2-carboxamido)acetic acid;
2-(3-hydroxy-1-oxo-5-(thiophen-2-yl)-1H-indene-2-carboxamido)acetic acid;
2-(3-hydroxy-1-oxo-4-(tetrahydro-2H-pyran-4-yl)-1H-indene-2-carboxamido)acetic acid;
2-(3-hydroxy-1-oxo-4-(pyridin-3-yl)-1H-indene-2-carboxamido)acetic acid; or
2-(3-hydroxy-1-oxo-4-(trifluoromethyl)-1H-indene-2-carboxamido)acetic acid.

14. A pharmaceutical composition comprising at least one pharmaceutically acceptable excipient, and a therapeutically effective amount of the at least one compound of claim 1.

15. The pharmaceutical composition of claim 14, wherein the at least one compound is present in an amount effective for the treatment of at least one disease selected from ischemia, anemia, wound healing, auto-transplantation, allo-transplantation, xeno-transplantation, systemic high blood pressure, thalassemia, diabetes, cancer, or an inflammatory disorder.

16. The pharmaceutical composition of claim 14, wherein the at least one compound is present in an amount effective for increasing the amount of erythropoietin in the blood of a subject.

17. A method for increasing the amount of erythropoietin in the blood of a subject, comprising: administering a therapeutically effective amount of the compound of claim 1 to the subject.

18. A method of increasing or stabilizing HIF levels or activity in a subject comprising administering to the subject the at least one compound of claim 1.

19. A method of modulating the amount of HIF in a cell, comprising contacting the cell with the at least one compound according to claim 1.

20. A method of inhibiting HIF hydroxylation in a subject, comprising administering to the subject the at least one compound according to claim 1.

21. A pharmaceutical composition, comprising a pharmaceutically acceptable carrier, excipient, or diluent, and at least one compound of Formula I:

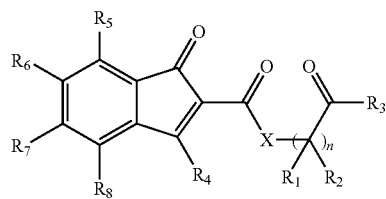

I or is a pharmaceutically acceptable salt thereof, a tautomer thereof, or a pharmaceutically acceptable salt of the tautomer; a chelate thereof, a non-covalent complex thereof, or a mixture of any of the foregoing, wherein:
n is 1 to 6;
X is $-NR_a-$, wherein $R_a$ is H;
each instance of $R_1$ and $R_2$ is independently selected from H, lower alkyl, substituted lower alkyl, lower haloalkyl, or substituted lower haloalkyl, or $R_1$ and $R_2$, together with the carbon to which they are attached, can join to a pharmaceutically acceptable salt thereof, a tautomer thereof, or a pharmaceutically acceptable salt of the tautomer; a chelate thereof, a non-covalent complex thereof, or a mixture of any of the foregoing, wherein:
n is 1 to 6;
X is $-NR_a-$, wherein $R_a$ is H;
each instance of $R_1$ and $R_2$ is independently selected from H, lower alkyl, substituted lower alkyl, lower haloalkyl, or substituted lower haloalkyl, or $R_1$ and $R_2$, together with the carbon to which they are attached, can join to form a 3-6 membered optionally substituted ring comprising 0, 1, or 2 heteroatoms selected from O, N, and S;
$R_3$ is selected from OH, SH, $NH_2$, lower alkyl, substituted lower alkyl, lower alkoxy, substituted lower alkoxy, or sulfanyl;
$R_4$ is OH;
$R_5$, $R_6$, $R_7$, and $R_8$ are independently selected from H, Cl, F, Br, I, alkyl, substituted alkyl, alkenyl, substituted alkenyl, alkynyl, substituted alkynyl, $NR_bR_c$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, haloalkyl, perhaloalkyl, or $-Y-R_{10}$, wherein:
Y is selected from $-N(R_{11})-Z-$ or $-Z-N(R_{11})-$;
Z is selected from C(O), $SO_2$, alkylene, substituted alkylene, alkenylene, substituted alkenylene, alkynylene, or substituted alkynylene;
$R_9$ is selected from H, alkyl, substituted alkyl, alkenyl, substituted alkenyl, alkynyl, or substituted alkynyl;
$R_{10}$ is selected from H, heterocyclyl, substituted heterocyclyl, aryl, substituted aryl, heteroaryl or substituted heteroaryl;
$R_{11}$ is selected from H, lower alkyl, or substituted lower alkyl; and
$R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring.

22. A method for inhibiting HIF hydroxylation in a subject, comprising administering to the subject a therapeutically effective amount of at least one compound of Formula I, wherein the compound of Formula I has the following formula:

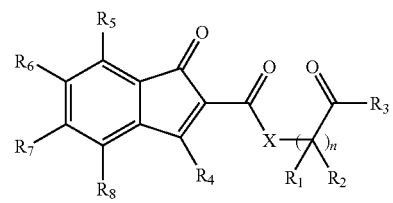

I or is a pharmaceutically acceptable salt thereof, a tautomer thereof, or a pharmaceutically acceptable salt of the tautomer; a chelate thereof, a non-covalent complex thereof, or a mixture of any of the foregoing, wherein:
n is 1 to 6;
X is $-NR_a-$, wherein $R_a$ is H;
each instance of $R_1$ and $R_2$ is independently selected from H, lower alkyl, substituted lower alkyl, lower haloalkyl, or substituted lower haloalkyl, or $R_1$ and $R_2$, together with the carbon to which they are attached, can join to form a 3-6 membered optionally substituted ring comprising 0, 1, or 2 heteroatoms selected from O, N, and S;

$R_3$ is selected from OH, SH, $NH_2$, lower alkyl, substituted lower alkyl, lower alkoxy, substituted lower alkoxy, or sulfanyl;

$R_4$ is OH;

$R_5$, $R_6$, $R_7$, and $R_8$ are independently selected from H, Cl, F, Br, I, alkyl, substituted alkyl, alkenyl, substituted alkenyl, alkynyl, substituted alkynyl, $NR_bR_c$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, haloalkyl, perhaloalkyl, or —Y—$R_{10}$, wherein:

Y is selected from —N($R_{11}$)—Z— or —Z—N($R_{11}$)—;

Z is selected from C(O), $SO_2$, alkylene, substituted alkylene, alkenylene, substituted alkenylene, alkynylene, or substituted alkynylene;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl or substituted heteroaryl;

$R_{11}$ is selected from H, lower alkyl, or substituted lower alkyl; and $R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring.

23. A method for increasing the amount of erythropoietin in the blood of a subject, comprising administering to the subject a therapeutically effective amount of at least one compound of Formula I, wherein the amount of erythropoietin in the blood of the subject is increased, and further wherein the compound of Formula I has the following formula:

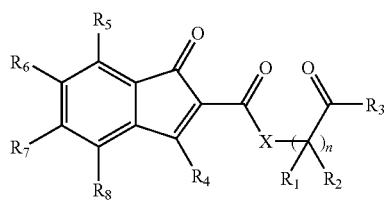

I or is a pharmaceutically acceptable salt thereof, a tautomer thereof, or a pharmaceutically acceptable salt of the tautomer; a chelate thereof, a non-covalent complex thereof, or a mixture of any of the foregoing, wherein:

n is 1 to 6;

X is —$NR_a$—, wherein $R_a$ is H;

each instance of $R_1$ and $R_2$ is independently selected from H, lower alkyl, substituted lower alkyl, lower haloalkyl, or substituted lower haloalkyl, or $R_1$ and $R_2$, together with the carbon to which they are attached, can join to form a 3-6 membered optionally substituted ring comprising 0, 1, or 2 heteroatoms selected from O, N, and S;

$R_3$ is selected from OH, SH, $NH_2$, lower alkyl, substituted lower alkyl, lower alkoxy, substituted lower alkoxy, or sulfanyl;

$R_4$ is OH;

$R_5$, $R_6$, $R_7$, and $R_8$ are independently selected from H, Cl, F, Br, I, alkyl, substituted alkyl, alkenyl, substituted alkenyl, alkynyl, substituted alkynyl, $NR_bR_c$, $C(O)OR_9$, $OR_9$, $SR_9$, $SO_2R_9$, CN, $NO_2$, aryl, substituted aryl, arylalkyl, substituted arylalkyl, heteroaryl, substituted heteroaryl, heteroarylalkyl, substituted heteroarylalkyl, heterocyclyl, substituted heterocyclyl, heterocyclylalkyl, substituted heterocyclylalkyl, alkoxycarbonyl, substituted alkoxycarbonyl, haloalkyl, perhaloalkyl, or —Y—$R_{10}$, wherein:

Y is selected from —N($R_{11}$)—Z— or —Z—N($R_{11}$)—;

Z is selected from C(O), $SO_2$, alkylene, substituted alkylene, alkenylene, substituted alkenylene, alkynylene, or substituted alkynylene;

$R_9$ is selected from H, alkyl, substituted alkyl, alkenyl, substituted alkenyl, alkynyl, or substituted alkynyl;

$R_{10}$ is selected from H, heterocyclyl, substituted heterocyclyl, aryl, substituted aryl, heteroaryl or substituted heteroaryl;

$R_{11}$ is selected from H, lower alkyl, or substituted lower alkyl; and $R_b$ and $R_c$ are independently selected from H, lower alkyl, substituted lower alkyl, lower haloalkyl, or substituted lower haloalkyl, or $R_b$ and $R_c$ can join together to form a 3 to 6 membered ring or a substituted 3 to 6 membered ring.

* * * * *